United States Patent [19]
Cairnes

[11] Patent Number: 6,139,494
[45] Date of Patent: Oct. 31, 2000

[54] METHOD AND APPARATUS FOR AN INTEGRATED CLINICAL TELE-INFORMATICS SYSTEM

[75] Inventor: Walter J. Cairnes, Vancouver, Canada

[73] Assignee: Health Informatics Tools, Vancouver, Canada

[21] Appl. No.: 08/953,852

[22] Filed: Oct. 15, 1997

[51] Int. Cl.[7] .................................................. A61M 5/00
[52] U.S. Cl. ........................................................ 600/300
[58] Field of Search ................................... 600/300, 301; 128/897, 898, 920–924; 705/2, 3

[56] References Cited

U.S. PATENT DOCUMENTS

| | | |
|---|---|---|
| 5,307,263 | 4/1994 | Brown . |
| 5,678,571 | 10/1997 | Brown . |
| 5,724,968 | 3/1998 | Iliff .......................................... 600/300 |
| 5,839,438 | 11/1998 | Graettinger et al. ..................... 600/300 |
| 5,897,493 | 4/1999 | Brown ..................................... 600/300 |
| 5,908,383 | 6/1999 | Brynjestad .............................. 600/300 |
| 5,954,641 | 9/1999 | Kehr et al. .............................. 600/300 |

Primary Examiner—Samuel G. Gilbert
Attorney, Agent, or Firm—Rader, Fishman & Grauer PLLC

[57] ABSTRACT

An integrated clinical tele-informatics based system that provides outpatient health care delivery, self-care services, clinical communications and information, and clinical practice management services. The system retrieves and analyzes sign and symptom data of patients according to a plurality of case management rules, generates a patient information and develops a therapeutic program in response to the information. The therapeutic program is regularly updated based upon system monitoring of the patient's condition. The system provides clinical management functional tools that alert a Personal Health Advisor when the data of at least one patient exceeds predefined medical parameters, triage clinical activity of volumes of patients based on the patient data, transform the data into clinical practice management information, and generate clinical practice management information reports of summarized text, numerical representations, and/or graphical representations.

20 Claims, 18 Drawing Sheets

MENU

MESSAGES
WEEKLY AGENDA
DEVICE CONNECT
MEDICAL LIBRARY
SOCIAL SERVICES
OTHER SERVICES
OTHER CONNECT (Sub-Category Examples)

| Messages | Weekly Agenda | Device Connect | Medical Library | Social Services | Other Services | Other Connect |
|---|---|---|---|---|---|---|
| Medications | | | MED. Terms | | | |
| Device Related | Calendar | Weight | Symptoms ID | Medical 1 | Medical | KYBD. I.S. |
| Lab Results | Therapies | Smart Cuff | MEDCTN DESC | Non-MED | Non-MED | KYBD, E.S. |
| Log Reports | | BLD-Glucose | | | | Monitor, ES |
| Interviews | | ECG | | | | |
| | | HRT Rate | | | | |

Fig. 8

METHOD AND APPARATUS FOR AN INTEGRATED CLINICAL TELE-INFORMATICS SYSTEM

BACKGROUND OF THE INVENTION

This invention relates to health care delivery in general and more specifically to tele-informatics that supports improved clinical case and clinical practice management in the outpatient setting.

Fundamental economic, legal and organization structure change in the health care industry, combined with the emerging predominance of long-term, non-acute outpatient medical conditions and needs such as chronic illness, rehabilitation and at risk pregnancy, require dramatically improved and cost-effective outpatient health care delivery and clinical practice management. This can only occur through more and better outpatient clinical communications and medical informatics. The proposed tele-informatics invention provides the requisite information technology system to enable health care organizations to accomplish these challenges.

The invention simultaneously provides or supports:

A systemic approach to outpatient care delivery and tele-informatics.

Integrated and comprehensive outpatient care delivery.

Efficient and productive clinical practice management.

Integrated and comprehensive clinical tele-informatics.

Medical specialty transcendence.

Anytime, anywhere care.

Health, versus disease, focused care and therefore proactive instead of reactive care.

Quality outcomes measurement.

Care, care delivery and tele-informatics standards.

A Care Delivery System for Today's Predominant Health Needs

The invention helps health providers deal with the new dominant clinical need in health care—the long term care and support of stable, non-acute outpatients who require monitoring and self-care. Such patients, who traditionally have been the most under-served clinical population, have become the heaviest users of health care resources. Examples include chronic illnesses—hypertension, asthma, diabetes, depression, pain; potentially controllable risk factors—dyslipidemia, diet related, substance abuse, obesity; conditions that require aggressive, integrated remote site monitoring—high risk pregnancy, congestive heart failure, post-operative conditions; conditions that require on-going patient/loved one education; first time pregnancy, infancy care; and rehabilitation needs including spinal cord injury and stroke.

These patients require cost-effective integrated and comprehensive care in their homes and workplaces. At the same time, health providers need a method for managing high volumes of such patients. The proposed invention fills these needs. The system enables care to be vastly improved by providing quality tele-informatics for effective sign and symptom surveillance, adherence monitoring and support, medications management, patient education and reinforcement, holistic patient care, timely responsiveness to changing conditions, care based on varying clinical need over long time periods through clinical case management and therapy integration.

Ideally, the quality of health care should not be affected by location and medical area—for example, hypertension management should be as effective as an invasive procedure. Similarly, the effect of other variables—including the patient's condition, when care is given, to whom care is given, from whom care is received or how long treatment is given—should be null. While efforts have been made to achieve this ideal of care delivery, current health care systems fall far short of these goals. The invention meets these challenges.

A Tele-Informatics System for Clinical Practice Management

Conventional care delivery fails to provide the clinical practice management needs of today's health care providers. Health providers, specifically clinical case managers, need to prioritize their time daily based on clinical need. Health providers work in an intense, high patient volume environment. This requires information technology tools that make work more productive, efficient and predictable. The invention accomplishes these tasks through a component called the Event Manager. For example, the invention organizes and plans a case manager's day based on each patient's condition and need for treatment while taking into consideration the health care needs of all patients of the health care providers that require attention. The system must survey patients signs and symptoms according to health care provider recommendations, and inform health care providers when data is expected, in, or late. Current health care delivery fails to provide health care providers these clinical management tools within a systemic context.

Promoting Quality Tele-Informatics

The invention provides a fully automated communication and informatics environment for the outpatient and their health providers. This promotes substantial improvement in both communications and information quality.

There are also challenges in providing clinical communications and information that meet qualitative and quantitative standards. The challenges include problems of asymmetric information, inert information, old information, information of dubious accuracy, non-standardized information, late or inadequate communications between patient and health provider, and between health providers, and non-usable information. Conventional health care information systems do not meet these clinical communications and information challenges—the invention addresses these needs.

SUMMARY OF THE INVENTION

The invention comprises a communications tele-informatics system for providing integrated and comprehensive outpatient care delivery, efficient and productive clinical practice management, and integrated comprehensive tele-informatics. The communications tele-informatics system transcends any particular health care specialty and provides consistent high quality health care regardless of the medical area involved, is highly flexible with respect to the number of patients associated to the system, and promotes active patient involvement in the patient's health care.

The communications tele-informatics system comprises a telecommunications server combined with a totally electronic informatics system which permits electronic clinical data functions and interactive communications between patients, Personal Health Advisors and health providers. The system is a turn-key system. It is an open system which is designed for simple connectivity to most major hospital based clinical information systems and is compatible with commercially available hardware.

The system includes at least one patient having an information appliance with an input capable of receiving medical device monitoring signals and an output adapted to be coupled to a telephone communications line. The information appliance is preferably in the form of a screen telephony information appliance and requires no computer facility on the part of a patient in order to participate in the exchange of information with the system.

Each patient is coupled to a Personal Health Advisor (PHA) having a computer workstation that includes at least one clinical software application, and is generally operated by a nurse. The PHA is bi-directionally coupled via a standard telephone communications line with a plurality of patients so that medical device signals generated at a given patient can be communicated to the Personal Health Advisor site for processing, and so that patient advisory information can be communicated from the Personal Health Advisor site to a given patient. A nurse is generally present at the PHA.

The system is highly flexible in that the number of patients associated with a Personal Health Advisor site can be expanded or contracted in accordance with demands. The Personal Health Advisor site has access to a wide variety of health providers, such as a primary care physician, a specialty physician, other health providers, a pharmacy, information services, a clinical lab, a hospital, and other services. Access to these health providers is afforded by a communications link between the Personal Health Advisor site and the health providers, which may be done by means of a local network or other communications links.

The system may also be locally customized to take into account local user preferences, including local medical and social cultures, all by changing the clinical software applications. Health care content, practice patterns and decision-making may be customized on this system.

By using standard telephone lines as a communications link, and an information appliance which is compatible with such telephone lines, the need for costly communications links, such as fiberoptic cables, high speed data lines and the like, is eliminated. In addition, the cost of connecting to the system is also minimized given the wide distribution of the public telephone network and the virtually universal accessibility to individuals.

The communications tele-informatics system of the present invention provides integrated and comprehensive outpatient care deliver, efficient and productive clinical practice management and integrated-comprehensive clinical tele-informatics. The health care system possesses the capability to support newly formed medical organizations which are geographically large. It supports the new focus of medicine: prevention, not disease, and is therefore proactive care, and not reactive care. It supports the new predominant type of disease: chronic illness, which requires care continuums, not episodes of care; enhanced self care and enhanced health provider care.

The communications tele-informatics system of the present invention includes sign and symptom surveillance, adherence monitoring and support, medications management, patient education and reinforcement, holistic patient care, timely responsiveness to a changing conditions, clinical risk and time continuums of care, comprehensive care, therapy integration and addresses issues of rurality of the patient.

The communications tele-informatics system of the present invention provides enhanced clinical practice management which provides a system and tools for effective clinical management of volumes of patient. The system optimizes individual patient care within the context of cost-effective high patient volume. The clinical practice management functionality is supported by event manager software.

As described herein, the present invention is a communications tele-informatics system for providing outpatient health care delivery, self-care services, clinical communications and information, and clinical practice management services, the system comprising: a first portion configured to accept medical sign and symptom data from a patient; a second portion configured to analyze the medical sign and symptom data entered in the first portion according to a plurality of clinical case management rules, and to generate the clinical information of the patient; a third portion configured to assign the patient at least one therapy responsive to the second portion clinical information; a fourth portion configured to provide a Personal Health Advisor the second portion clinical information and the at least one patient therapy; and a fifth portion configured to monitor further medical signs and symptoms of the patient and to provide clinical information update of the patient; and a sixth portion configured to provide clinical practice management of a plurality of patients to a Personal Health Advisor wherein the medical sign and symptom data is transformed into clinical practice management information.

As further described herein, the invention includes a method for providing a communications tele-informatics system for providing outpatient health care delivery, patient self-care services, clinical communications and information, and clinical practice management services, the method comprising the following steps performed by a Personal Health Advisor, of: retrieving medical sign and symptom data from the patient; analyzing the medical sign and symptom data of the patient according to a plurality of clinical case management rules; generating clinical case management information of the patient from the analyzing step; assigning the patient at least one therapy responsive to the generating step; sending to the patient the at least one therapy of the assigning step; and providing clinical practice management of a plurality of patients wherein the medical sign and symptom data is transformed into clinical practice management information including at least one from the group of summarized text, numerical representations and graphical representations.

For a fuller understanding of the nature and advantages of the invention, reference should be made to the ensuing detailed description, taken in conjunction with the accompanying drawings.

BRIEF DESCRIPTION OF THE DRAWINGS

FIG. 8 illustrates a patient software function list provided by the system of FIG. 1.

DETAILED DESCRIPTION OF THE PREFERRED EMBODIMENTS

Figure 1:
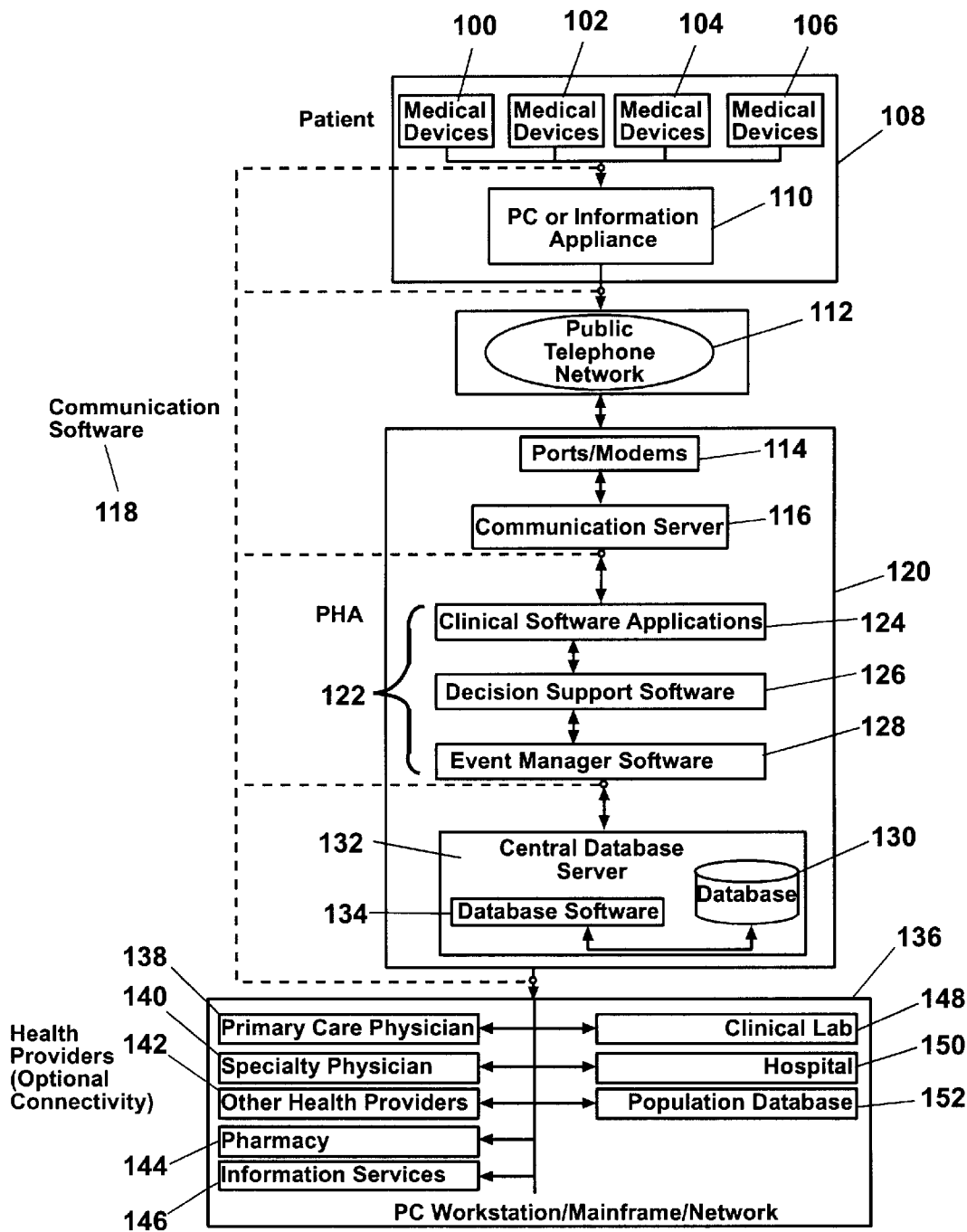
FIG. 1 is a schematic block diagram of an integrated clinical tele-informatics system in accordance with a preferred embodiment of the present invention.

Turning now to the drawings, FIG. 1(a) is a schematic system block diagram illustrating a preferred embodiment of the invention. As seen in this figure, the system involves the interaction between a patient 108, a Personal Health Advisor ("PHA") 120 and one or more health providers 136. Although one patient is shown, the system may include a plurality of patients. Patient 108 uses a personal computer or information appliance 110 described more fully below, and one or more medical devices 100, 102, 104 and 106, which are used to monitor physical patient symptoms. Representative examples of medical devices 100, 102, 104 and 106 are a blood pressure cuff, a weight scale, a heart rate monitor, and a blood glucose monitor. Other such devices will occur to those skilled in the art. Each device is capable of generating analog or digital electrical signals representative of the value of the physical patient parameter being measured by the device. Each medical device 100, 102, 104, and 106 is also provided with a suitable interface, whether hardwired or cordless, enabling the medical device signals to be in 2-way communications with the information appliance 110.

Patient 108 and PHA 120 are interconnected for two-way communications using communications software 118 that resides both at the location of patient 108 and PHA 120. Communication generally takes place by means of public telephone network 112 since this is the most widely available communications link. Example preferred embodiments of a communications link are hardwired, cellular, or digital transmissions over the telephone network 112. Conventional data ports and modems 114 and a communications server 116 are provided at PHA 120 to enable the transfer of information between the information appliance 110 over the public telephone network 112 to PHA 120. Communications server 116, along with data ports/modems 114, permit a large number (e.g., several hundred) of patients 108 to simultaneously communicate with a single PHA 120.

PHA 120 includes a suitable work station, preferably a personal computer 122. As illustrated in FIG. 1(a), the work station 122 of PHA 120 includes one or more clinical software applications 124, decision support software 126 and event manager software 128. Database software 134 generates a local database 130 which supports an outpatient tele-informatics data medical profile system. If not part of workstation 122, database 130 may reside on a separate central database server 132 which provides the underlying database software 134 for tele-informatics database functions. Possible database software includes Microsoft® Access.

PHA 120 has two way access to a plurality of optional health providers and other sites 136, such as the primary care physician 138 for an individual patient, a specialty physician 140 for special consultation purposes, other health providers 142, a pharmacy 144, an information services site 146, a clinical lab 148, a hospital 150, and a population database 152. The health provider sites 136 may all include individual personal computer workstations, or may be under the control of a mainframe computer or accessible over a network such as telephone network 112.

Figure 2:
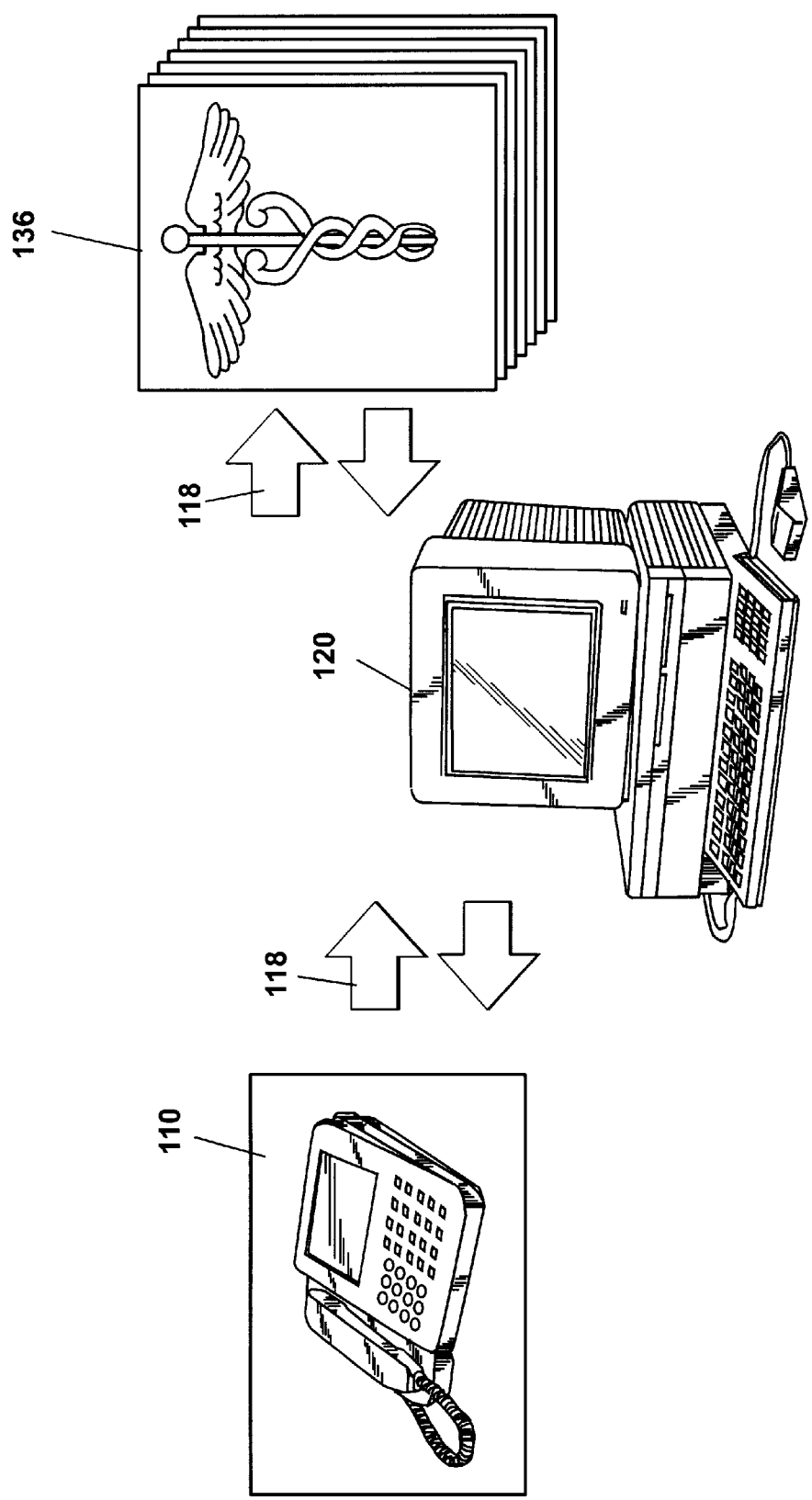
FIG. 2 shows a diagram of the information appliance incorporated within the system of FIG. 1.

Thus, as shown in FIG. 2 a patient 108 is interconnected with a PHA 120 by means of information appliance 110 and communications software 118. Similarly, PHA 120 is interconnected with a health provider 136 by means of communications software 118. The communications software 118 resides on information appliance 110, workstation 122 or communications server 116 of PHA 120, and on the system of health provider 136. As a result, patient 108 may constantly interact with PHA 120 and health provider 136 while PHA 120 and health provider 136 may closely monitor the patient's condition. The interaction between decision support software 126, event manager software 128 and database 130 provide PHA 120 and health providers 136, by means of information appliance 110 and communications software 118, a tele-informatics system to perform constant sign and system surveillance of patients 108.

Figure 3:
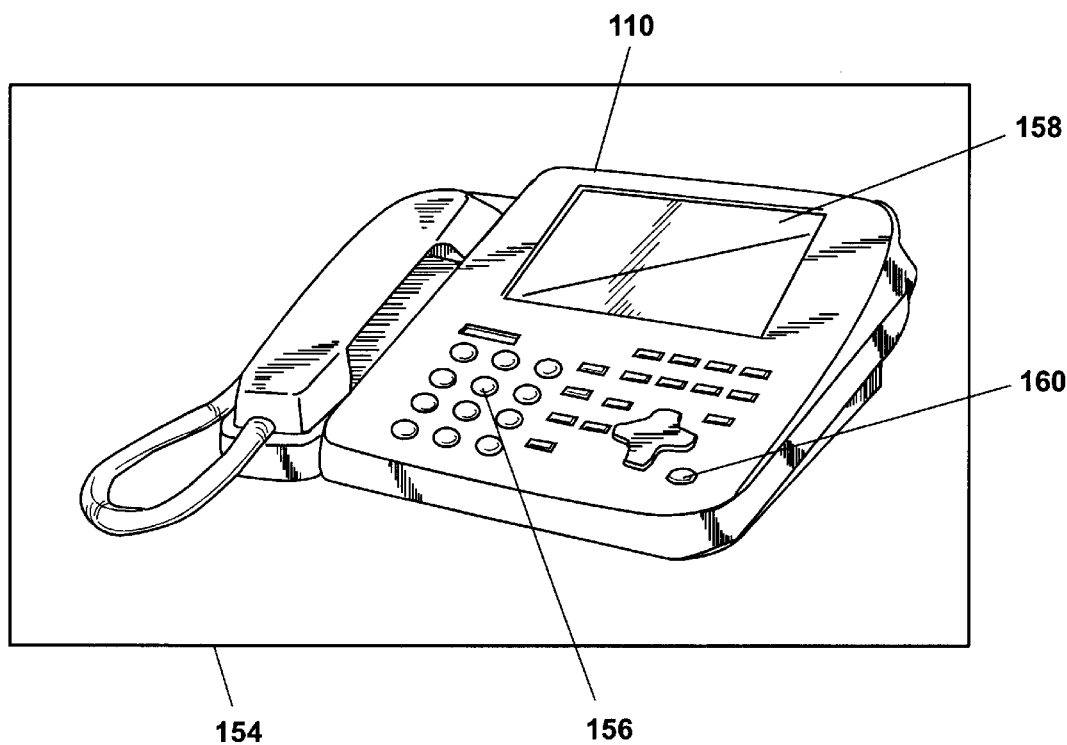
FIG. 3 illustrates a preferred embodiment of the information appliance installed at the patient of the system of FIG. 1.

At the location of a patient 108, information appliance 110, shown in detail in FIG. 3, is preferably a user friendly device. Although a touch screen information appliance is shown, other embodiments may preferably include a screen telephony information appliance that does not include a touch sensitive screen, or be a personal computer. Information appliance 110 includes a telephone handset 154, a data entry device such as a keyboard 156, a alphanumeric display 158, and a message light 160. Keyboard 156 has the usual 12 key keypad as well as function keys for enabling selection of display menus in response to screen prompting. The message light 160 flashes on and off when one or more messages are awaiting patient review. One possible information appliance 110 is an expanded function telephone device, referred to as a "Smartphone", available from the Forval Corporation. A Smartphone is a microprocessor based intelligent telephone set having an optional touch sensitive screen 158, an embedded modem, external connectivity to analog telephone lines, and suitable interfaces to enable various medical devices 100, 102, 104 and 106 to be connected thereto, such as by means of a serial port interface. Thus, the medical devices are also data entry devices. The use of an information appliance such as that shown in FIG. 3 is preferred to permit technologically unsophisticated patients to fully interact with the system without the need for sophisticated computer training.

Information appliance 110 has been selected because the software based patient user interface installed on the device increases the probability of consistent patient usage by providing simplicity of use, patient convenience, reliability, durability, aesthetic appeal, and ease of installation.

Additionally, information appliance 110 has been found to be cost effective, well tested, and yet still capable of standard computer and telephone functions. To the patient, the information appliance 110 appears as an attractive telephone with additional easy to use features. Information appliance 110 incorporates software designed in such a manner that the patient need not use commands, computer keyboards or learn computer terms. Interactions are as simple as those with an automatic teller ("ATM") machine, and the patient can easily operate the device such as by touching areas of touch sensitive screen display 158 to interact with the entire system. Thus, the patient may access information about the patient's illness, receive regular treatment routines based on a specific condition, be prompted for purposes of therapy adherence, and receive symptom or medical data surveillance by a PHA 120. Information appliance 110 is thus the heart of the system from the perspective of the patient.

Figure 4:
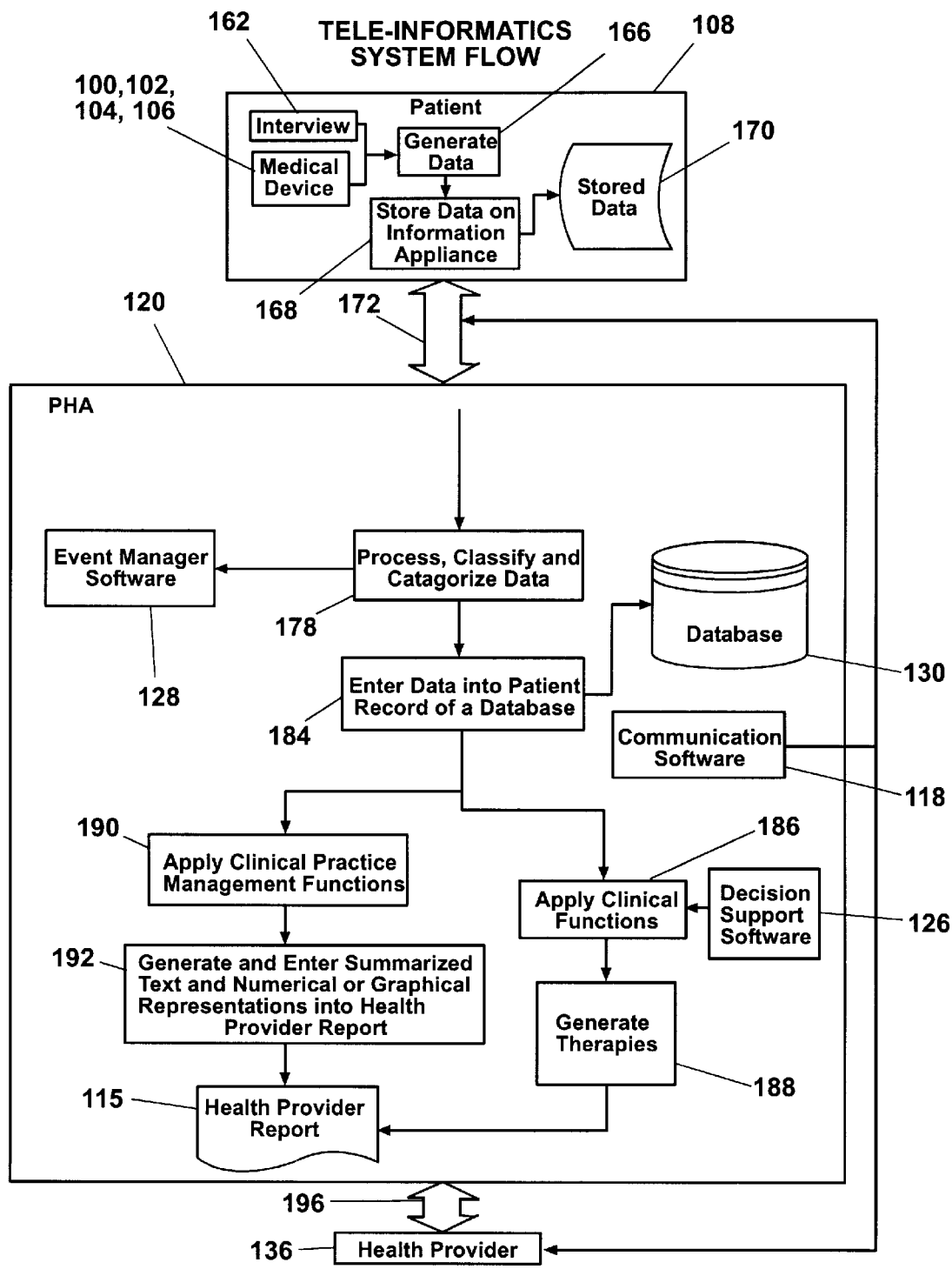
FIG. 4 is a schematic block diagram of the flow, classification, and categorization of data that a patient enters which is subsequently converted to information for clinical practice management, care delivery, and clinical communications and information in accordance with the integrated clinical tele-informatics system of FIG. 1.

FIG. 4 is a schematic block diagram of the flow, classification, and categorization of data that a patient enters which is subsequently converted to information for clinical practice management, care delivery, and clinical communications and information in accordance with the integrated clinical tele-informatics system of FIG. 1. The figure provides an overview of the flow and conversion of data on the integrated clinical tele-informatics system of FIG. 1.

In step 166, patient 108 generates medical data by means of an electronic interview 162 and/or a medical device 100, 102, 104, 106. In a preferred embodiment, the data generally includes the patient's vital signs and symptoms. Alternative embodiments may generate additional types of data. In step 168, the data is stored as shown at point 170 on information appliance 110.

In step 172, patient 108 transmits the stored data to PHA 120 as discussed above. In step 178 the event manager software 128 processes, classifies and categorizes the data. As shown at point 184, the data is then entered in a patient record of database 130.

In step 190, PHA 120 may choose to apply clinical practice management functions to triage patients to prioritize and manage the disbursement of health care to volumes of patients. Execution of the functions generate value added information including summarized text, and numerical or graphical representations as shown at point 192. Although not shown, this information may automatically calendar activities into the health providers and/or PHA's schedule. The information may electronically update a PHA and/or health provider report 115.

In step 196, the PHA may automatically transmit one or more health provider report to each health provider 136. The transmission of the information is supported by communications software 118 resident at PHA 120 and health provider 136.

In step 186, the PHA may choose to apply clinical functions to the patient record stored on the database 130. Executing clinical functions supported by the decision support software 126 generates therapy information 188 of recommended treatments for patients. The information may be automatically entered into a PHA and/or health provider report 115.

Decision support software 126 typically resides in work station 122 of PHA 120. Software 126 recommends therapies based upon an analysis of sign and symptom data a patient 108 sends to PHA 120. Software 126 may be individually tailored to meet the informational requirements of a PHA 120, health providers 136, and patients 108. For example, a preferred embodiment of the present invention may recommend therapies according to standards set by a particular national medical organization and/or institute. Thus, PHA 120 and health providers 136 may customize the preferred recommendations in suggesting health care options.

Computerized therapeutics facilitate system-wide prevention therapeutics so that health care providers 136 and PHA 120 have available therapies conducive to each patient's needs. With appropriate updates to decision support software 126 it is possible to customize and update, on an on-going basis, preferred recommendations with newly available therapies.

Figure 7:
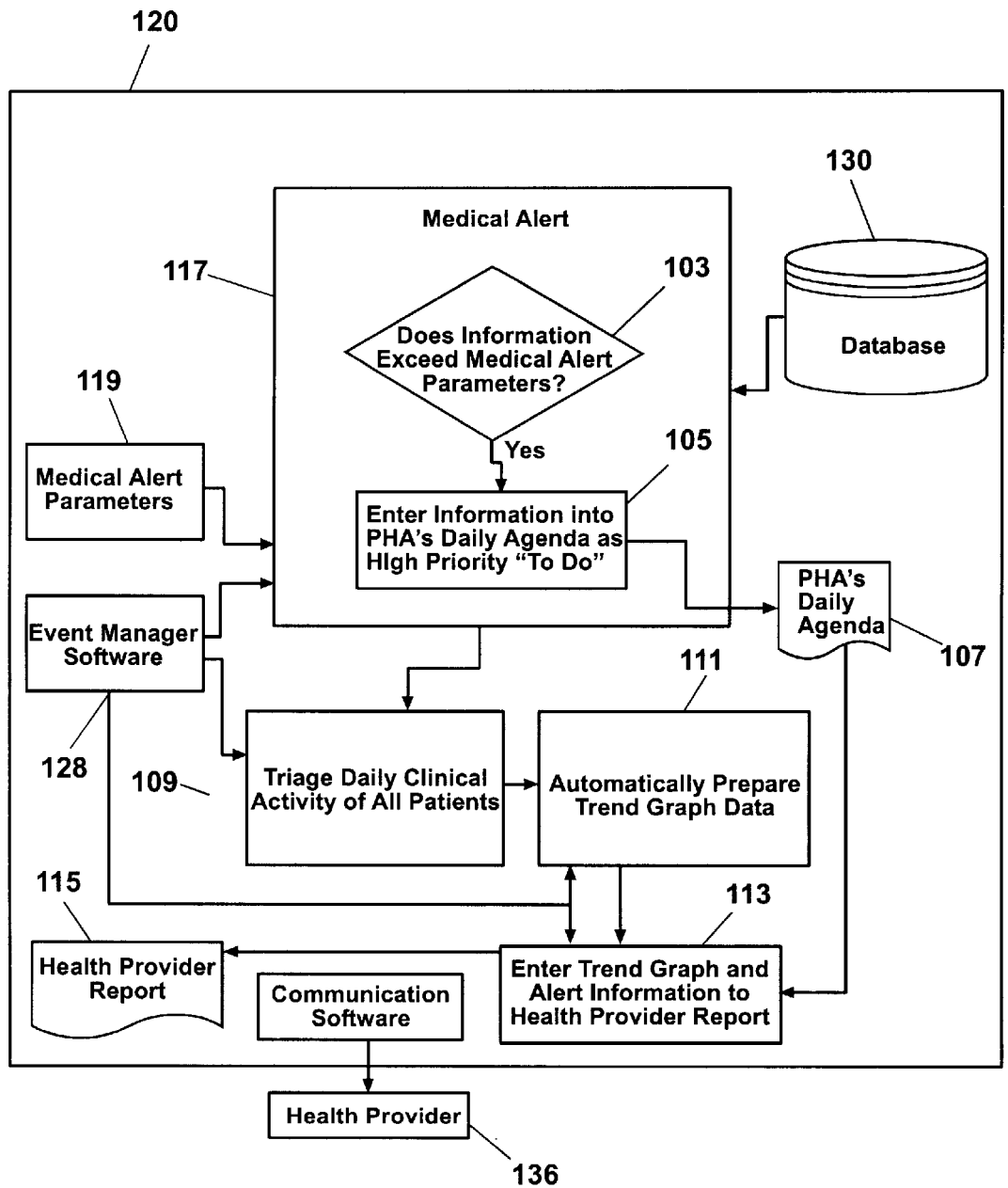
FIG. 7 is an example diagram of the execution of clinical practice management functions of FIG. 6 that enable a PHA and a health provider to manage volumes of patients.

FIG. 7 illustrates a sample health data list 300 that may be supported by database 130 for patients 108, PHA and health providers 136. Examples of available clinical related information for PHA 120 include health risk factor data, epidemiology data, medication data, medical library information, demographics, patient profiles, patient medical history and lab results. Examples of data 300 for patients 108 and health provider 136 are shown in the figure.

Figure 5:
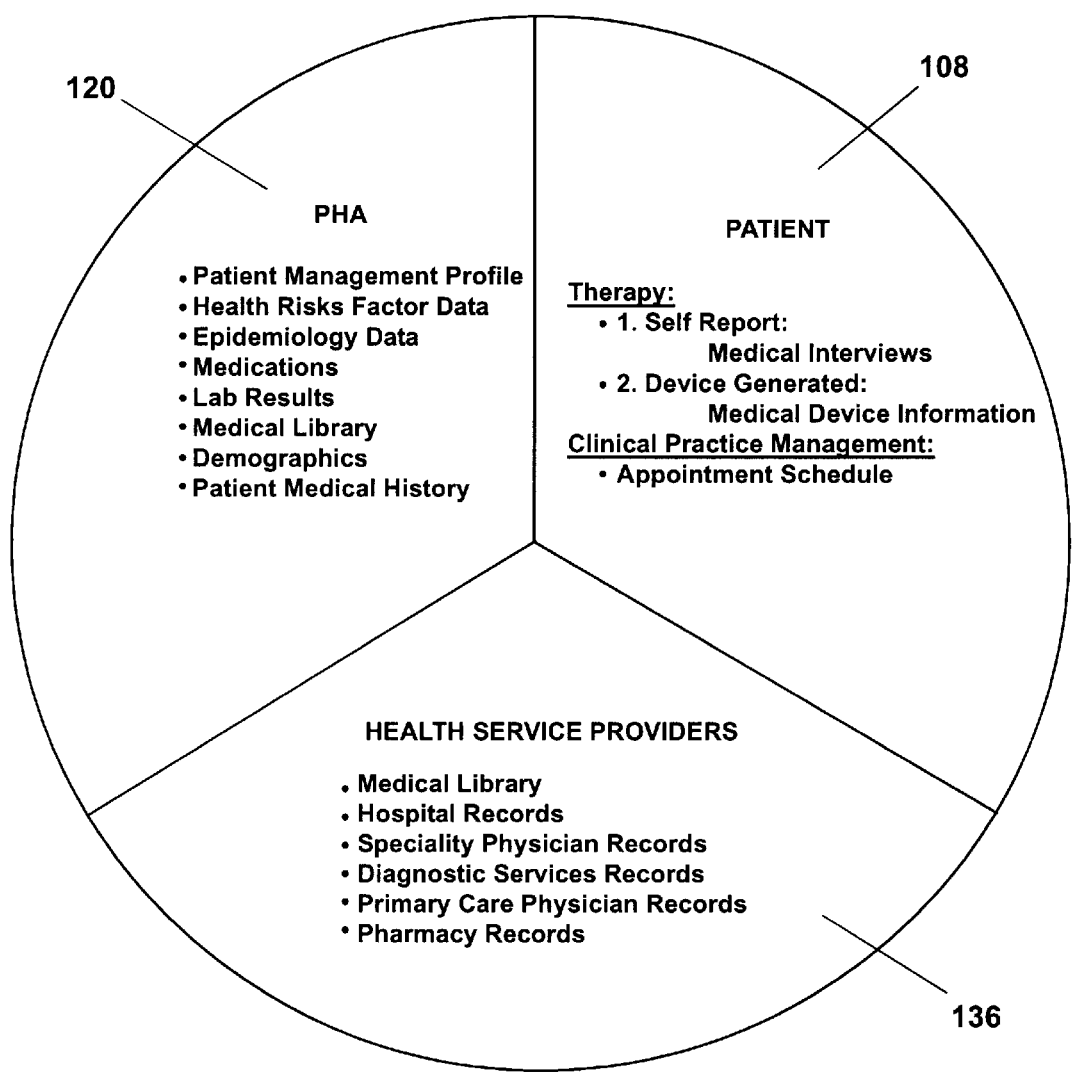
FIG. 5 is an example of data entered into the system of FIG. 1.

The data list example of FIG. 5 is provided only for illustrative purposes and should not be construed in a limiting sense. The types of data required may be easily customized to meet the specific needs of each patient 108, PHA 120, and health provider 136. The system is easily modified with respect to both the data it captures and the decision support it provides to meet the clinical management needs of patients 108, PHA 120, and health service provider 136.

To assist a health provider 136 in managing a healthcare practice including trends among various patients having similar conditions, the present invention calendars, prioritizes and organizes the health care provider's schedule by triaging patients to determine each patient's current condition and health care needs.

Figure 6:
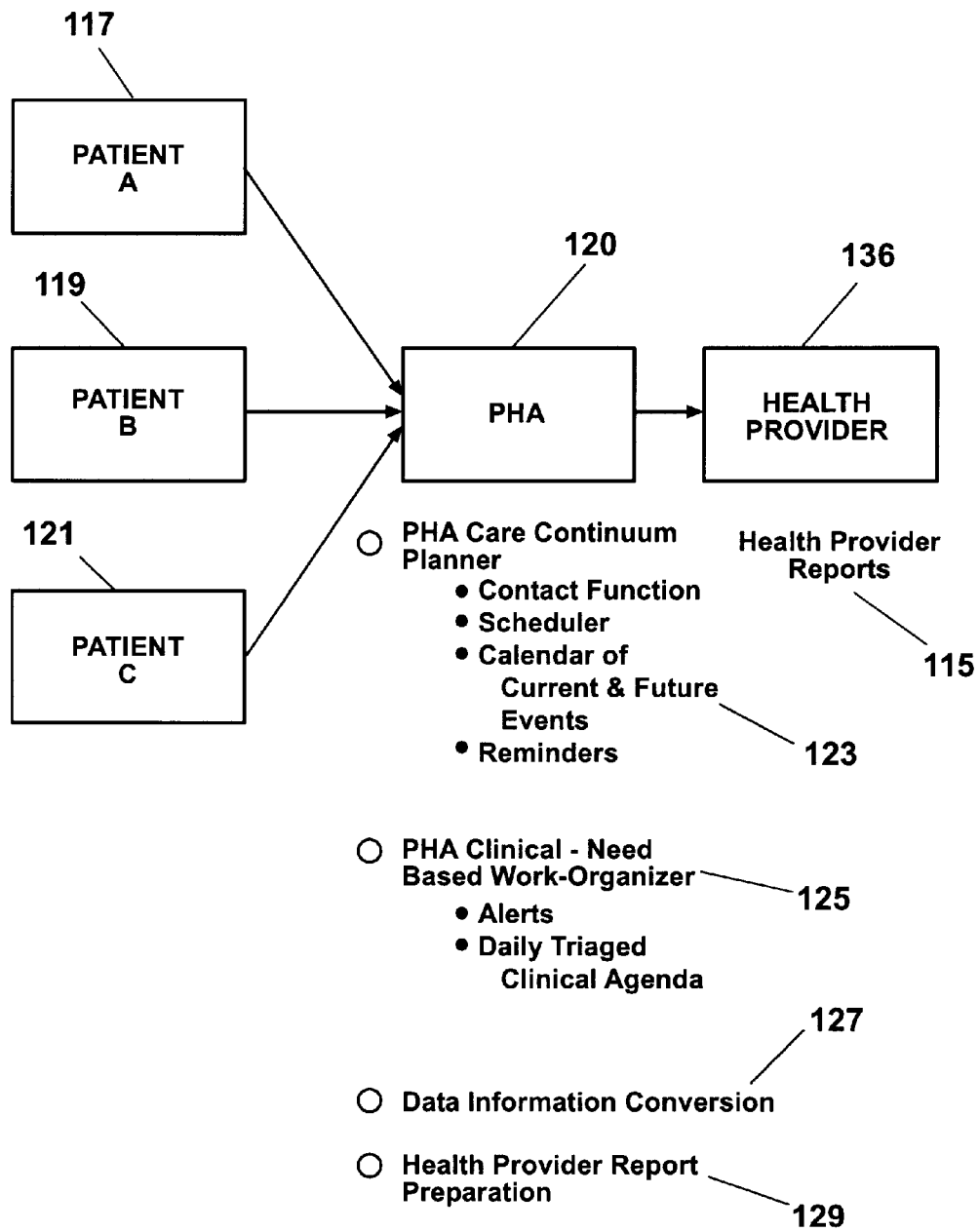
FIG. 6 is an example diagram of the clinical practice management functions that enable a PHA and a health provider to manage volumes of patients.

FIG. 6 is an example diagram of the clinical practice management functions that enable a PHA and a Health Provider to manage volumes of patients. As shown at points 117, 119, and 121, respectively, three patients 108, namely patient A, patient B, and patient C send PHA 120 vital sign and symptom survey medical data generated by data entry medical devices 100, 102, 104, 106 or through electronic interviews and stored by information appliance 110. PHA 120 processes the data provided by the patients 108 to automatically generate clinical management reports pursuant to a plurality of clinical management functions.

One function, the PHA Care Continuum Planner 123, manages over time, based upon need and routine care, the daily health care of a plurality of patients. The event manager software 128 of PHA 120 prioritizes patient care by comparing data received from each patient. Thus, the event manager software 128 categorizes and classifies data each day for PHA 120 based on what is important for the PHA to know and to do. The PHA Care Continuum Planner 123 includes a contact function, a scheduler, a calendar of current and future events and reminders.

Another function, the PHA Clinical-Need Based Work-Organizer 125 provides PHA 120 medical alerts and a daily triaged clinical agenda. A medical alert is generated when PHA 120 processes patient data and identifies that at least one sign and symptom of a patient exceeds predefined medical parameters. The alert is entered in the PHA's daily agenda as a high priority "to do." A daily triaged clinical agenda is generated from a comparative analysis of the information provided by each patient. The agenda prioritizes the PHA's response to each patient's health care needs. Another function, the Data Information Conversion function 127 converts raw sign and symptom medical data provided by a patient 108 to useable information in any practical context. Raw sign and symptom medical data is entered from medical devices 100, 102, 104, 106, and from reports generated from patient electronic interviews. Patients send the medical data to the PHA. The nurse at PHA 120 pre-selects data for conversion and the Data Information Conversion Function 127 transforms the data into summarized text, and numerical or graphical representations.

Another function, the Health Provider Report Preparation function 129 provides a nurse at a PHA 120, or physician at a health provider 136, a means for pre-selecting the information he or she wants to enter into a report, and when, where and to whom it is to be sent.

FIG. 7 is a diagram of an example execution of clinical practice management functions of FIG. 6 that enable a nurse at a PHA 120, and a health provider 136 to manage volumes of patients. Although not shown, in FIG. 7, PHA 120 has received medical data from patients 108. Once received, the data was processed, classified, categorized and entered into a patient record of database 130.

As shown in step 103 of FIG. 7, alerts are generated when information entered into a patient record of database 130 exceeds pre-defined medical parameters 119. When the information exceeds pre-defined medical parameters 119, in step 105, the event manager software 128 copies the information from the database 130, (a patient and the patient's irregular sign or symptom) into the PHA's Daily Agenda 107 as a high priority "To Do".

In step 109, the event manager software 128 triages daily clinical activity of entered patient data. In step 111, the event manager software 128 prepares a trend graph (data information conversion). In step 113, the event manager software 128, enters the trend graph and the alert information into one or more health provider reports 115. The health provider reports are sent to one or more health providers 136.

Database software 134 supports the tele-informatics database functions. It provides functions to collect, update and maintain outpatient tele-informatics data. It supports the data entered by patients 108 by means of information appliance 110, PHA 120 and health providers 136.

Event manager software 128 provides automated processing and integration of information the patients 108, PHA 120 and health providers 136 enter into the tele-informatics system of FIG. 1. It supports automated processing of the tele-informatics system's clinical applications and clinical practice management. When PHA 120 receives patient data, event manager software 128 analyzes, classifies and categorizes the data. Database software 134 stores and updates the analyzed patient data in database 130. The event manager software 128 informs health care providers when survey data of patient signs and symptoms is expected, when it arrives, or when it is late.

The clinical practice management functions may be used by PHA 120 and health providers 136 to convert patient information to value-added information. For example, execution of one clinical practice management function electronically triages a patient 108 to identify the patient's condition and comparative need for health care with respect to other patients. Another clinical function calendars the information into a health provider schedule.

In response to information provided by a patient 108 using devices 100, 102, 104, 106 and responses to queries, PHA 120 processes, classifies and categorizes patient entered data and generates recommended clinical related information such as therapies. Once data processing ends, PHA 120 and health providers 136 may automatically receive clinical practice management information, such as appointment schedules and triaged information. For example, the health care providers may be alerted to patients which require immediate treatment, and may receive a daily schedule based upon a comparative analysis of prior scheduled commitments, routine patient care and emergency health care. PHA 120 and health providers 136 use the information to manage their clinical practices.

FIG. 8 illustrates a patient software function menu seen by a patient 108 using information appliance 110 as illustrated in FIG. 2. The sample menu includes a list of categories which may be called up by simply touching the screen adjacent to the particular category.

Figure 9:
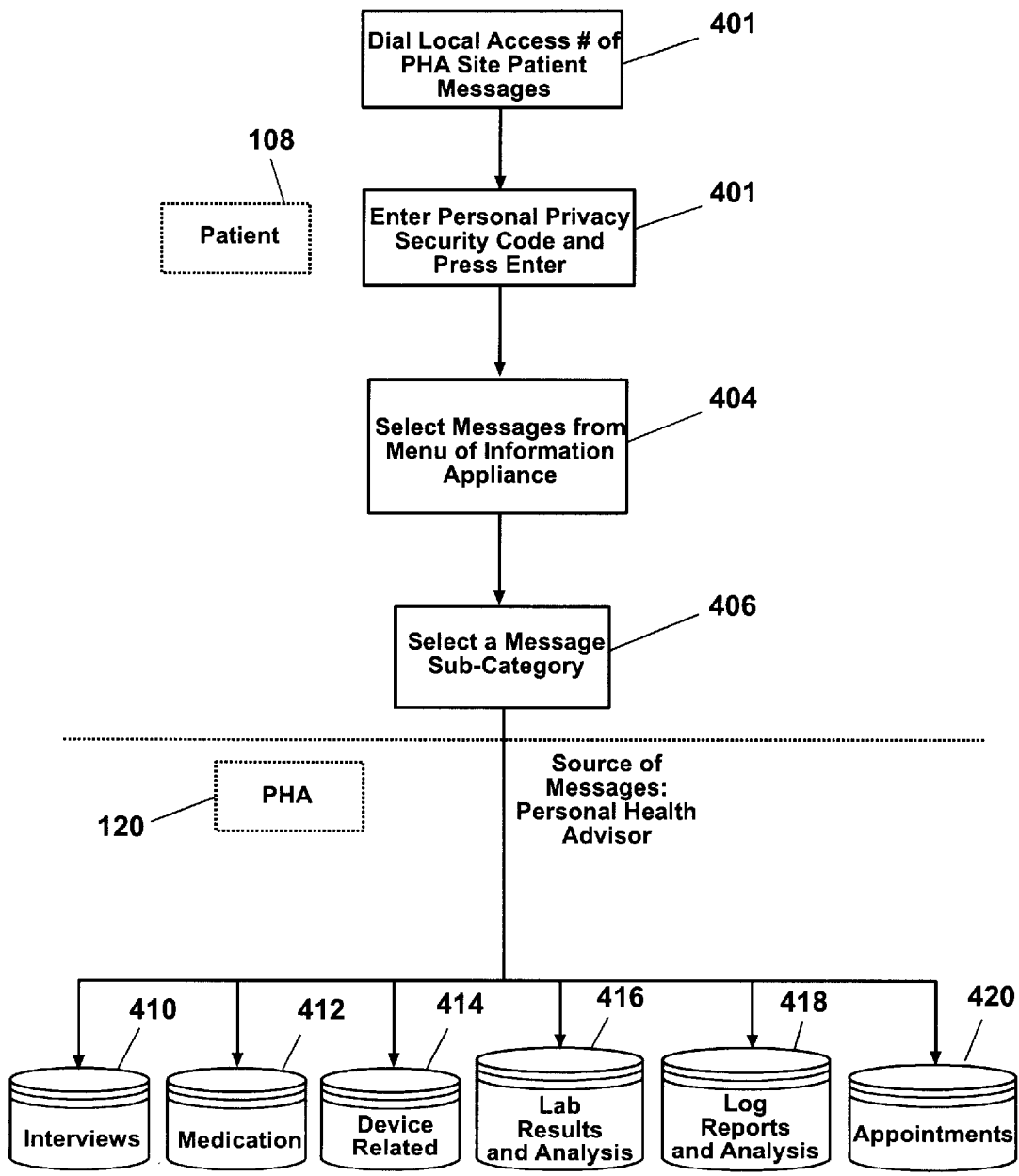
FIG. 9 is a flowchart showing an example of patient messages transmitted over the system of FIG. 1.

FIG. 9 is a flowchart showing a preferred embodiment of the process a patient 108 follows to access PHA 120. A patient 108, in step 401, dials a local access number to PHA 120. In a preferred embodiment, a modem internal to the information appliance 110 attempts to establish 2-way communications over public telephone network 112 with PHA 120 by means of communications software 118, data ports/modems 114, and optional communications server 116 associated with PHA 120. Once communications is established, in step 402, patient 108 enters a personal privacy security code on display 158 of FIG. 2. If entered incorrectly, the system queries the patient to re-enter the security code. After three failed access attempts, the system locks the patient's account and informs patient 108 to call PHA 120 for further assistance.

If patient 108 correctly enters the security code, the information appliance 110 displays a menu screen of the available menu choices shown in FIG. 8. If the patient selects "MESSAGES", in step 404, the system provides a sub-menu of message categories. In step 406, patient 108 selects a message category, as described in FIG. 8. In a preferred embodiment, the messages provided by PHA 120 include interviews 410, medications 412, device related 414, lab results and analysis 416, log reports and analysis 418, and appointments 420. The example of available messages subcategories is provided only for illustrative purposes and should not be construed to limit message types available in the system of FIG. 1. Generally, the device related 414, interview 410 and appointment messages 420 are used to obtain patient data, while other message types may inform patient 108 of the patients condition, therapies, and other pertinent health information.

More specifically, the purpose and function of the various subcategories listed for the menu choices of FIG. 8 are as follows:

MESSAGES MENU

Medications (MEDS)

A nurse operating the workstation at PHA 120 can input data about medications. The functions include initiating, changing, and terminating a medication, its dosage and frequency. This data can then be transmitted to patient 108.

Device Related

A nurse can input data at PHA 120 about devices 100, 102, 104, 106 that connect to information appliance 110 and transmit the data to a patient 108. The functions include initiating, changing and terminating device usage, as well as the type of device and date, time and frequency of usage.

Lab Results and Analysis

PHA 120 may electronically receive data from a lab, and transmit it to a patient 108. A nurse at PHA 120 can also input an interpretation of the lab data to assist a patient 108 in understanding the meaning of the data.

Log Reports and Analysis

Data is generated by devices 100, 102, 104, 106 or PHA 120 and can be transmitted between PHA 120 and a patient 108 as discussed above. PHA 120 can also input and transmit an interpretation of the data to assist patient 108 in understanding the meaning of the data. Data can be formulated in both table and graph formats.

Appointments

A nurse at a PHA120 can input data to various appointment sub-categories such as "Appointment Setting" and "Appointment Reminder". "Appointment Setting" may permit two-way communications. For example, a patient 108 may select from several available appointment schedules that have been structured by PHA 120. In contrast, an "Appointment Reminder" is typically a one-way communication from PHA 120 to patient 108.

Interviews

A nurse at a PHA 120 can transmit a series of questions about a particular clinical state to a patient 108. The purpose of such a query is to generate self-report medical data from patient 108. The resulting responses can assist the nurse of PHA120 in symptom surveillance, patient adherence to therapies and other patient and clinical state management functions. In some cases a specific response to a query may result in device 110 immediately notifying a patient 108 to contact the nurse at PHA 120 or the nurse to immediately contact patient 108.

WEEKLY AGENDA MENU

WEEKLY AGENDA is an organizer for a patient 108. This function has important medical implications—it integrates health care delivery. The application takes all the various medical "things" that a patient 108 or a loved one assisting a patient 108 must do on a regular basis. It also helps a nurse at a PHA 120 to ensure that there are no conflicting therapies issued from different physicians that could harm a patient.

WEEKLY AGENDA has a temporal component. While illustrated as being weekly, it can be set up for any time period depending on the clinical state and the patient's needs. There are two sub-categories: "Calendar" and "Therapies". "Calendar" may include two further sub-categories such as "Week of" or "Future" content for a time period following the upcoming week. "Week of" includes a time and date schedule of appointments, interviews, device usage. "Future" is primarily for appointments covering a subsequent four week period.

"Therapies" are communicated from a PHA 120 to a patient 108 to provide patient 108 with a weekly routine, "Therapies" may include such further subcategories as "Medications", or various risk factor modification applications, including ones on smoking cessation, diet, exercise and stress management.

DEVICE CONNECT MENU

The use of devices 100, 102, 104 and 106 are discussed above. Examples of such devices include a weight scale, smartcuff, heart rate monitor, blood-glucose monitor and ECG. By means of the Device Connect Menu a patient 108 can transmit data from patient-site based medical devices to the information appliance 110. DEVICE CONNECT permits patient 108 to plug the device into a jack in the back of the information appliance 110 and record the transmission from the device (e.g. 100, 102, 104 or 106) to the information appliance. The data is subsequently transmitted from the appliance 110 to PHA 120. A cuff, for example, communicates blood pressure to the appliance 110—the reading is displayed to patient 108 and also transmitted to PHA 120. This communication is from device to information appliance 110 to PHA 120.

MEDICAL LIBRARY MENU

A patient 108 can access simple, concise information about disease states, therapies and treatments, wellness and prevention, symptoms, and medical drugs. The sample sub-categories include "Medical Terms", "Symptom Identity", and Medication Description" The system for each menu selection can include a question and answer format.

Figure 10:
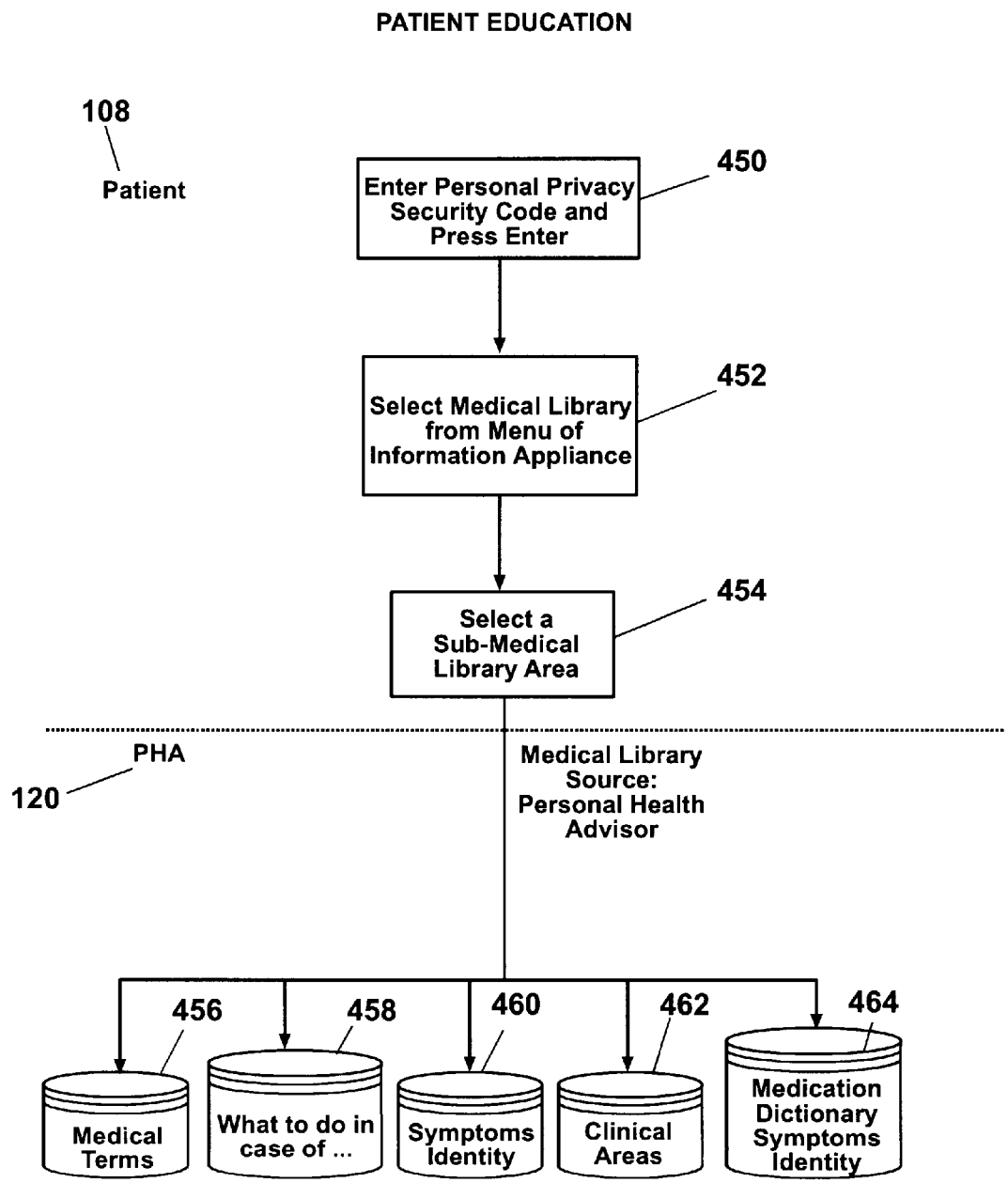
FIG. 10 is a flow chart showing an example of patient education provided by the system of FIG. 1.

FIG. 10 is a flowchart showing an example of "Patient Education" provided by the system of FIG. 1. when menu choice MEDICAL LIBRARY is selected by a patient 108 in FIG. 8. Educating a patient 108 of their medical condition is an important aspect of each patient's therapeutic program. The system of FIG. 1 satisfies this important need by electronically providing patient 108 access to a medical library of educational materials. In step 450, patient 108 enters a personal privacy security code on the patient's information appliance 110. In step 452, patient 108 selects "Medical Library" from the menu of available options. In step 454, patient 108 selects a specific medical area. In a preferred embodiment, the electronic medical library of the PHA will include topics such as medical terms 456, "what to do in case of . . . "458, symptoms identity 460, clinical areas 462, and medication dictionary symptoms identity 464. Patient 108 selects and reads informative educational material so that the patient may better understand the patient's medical condition and the comprehensive therapies the patient may receive from PHA 120 or health providers 136.

SOCIAL SERVICES MENU

A patient 108 can access ongoing social-based provider generated information/services that are both medical and non-medical based including an electronic version of information from organizations such as Mended Hearts. Connectivity can be local or national in scope. The communications is typically from PHA 120 to patient 108.

OTHER SERVICES MENU

OTHER SERVICES permit the use of additional on-line services.

Medical

"Medical" can include such services as "Clinical Records", "Financial Records", and "Medical Directory". These type of services are typically required by provider/payer organizations.

Non-medical

"Non-medical" can include standard on-line commercial transaction activities such as "Banking", "Shopping" "Travel" services, etc. "Non-medical" services are available through commercial organizations on a monthly fee basis. "Non-medical" services could be localized because the system is comparable to a private, locally based on-line service.

OTHER CONNECT MENU

OTHER CONNECT permits other external devices to be connected to the information appliance 110. Ports are already available for connectivity. Example subcategories include keyboards, both internal and external, an external monitor, and external printer.

SPECIFIC EXAMPLES OF SYSTEM USAGE

FIGS. 11–17 are flowcharts illustrating specific examples of patient 108, PHA 120 and health provider 136 use of the clinical management and clinical practice management functions available in the tele-informatics system of FIG. 1.

Figure 11:
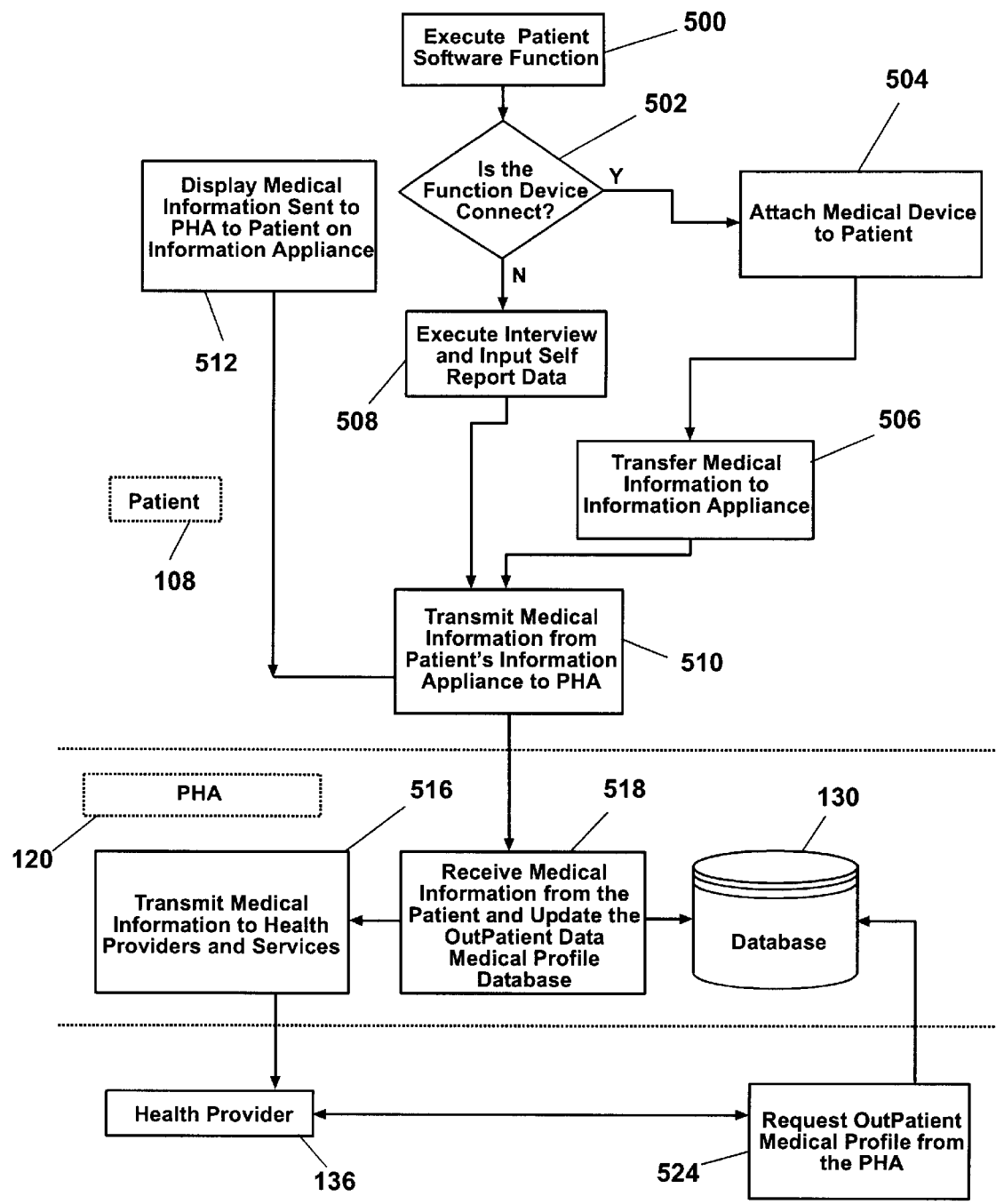
FIG. 11 is flowchart showing an example of "Sign and Symptom Surveillance" provided by the system of FIG. 1.

FIG. 11 is flowchart showing an example of "Sign and Symptom Surveillance" of patient 108, where a PHA 120 monitors a patient's medical condition. Although not shown, patient 108, first establishes a connection to PHA 120 via information appliance 110 as discussed above. Once appropriate communications is established, patient 108, in step 500, executes a software function to enter information regarding the patient's medical condition.

In step 502, if patient 108 transmits medical device information, patient 108 selects the software function "DEVICE CONNECT" from the display menu, and then selects the type of medical device the patient will use to obtain medical condition information, such as weight, smart cuff, blood glucose, ECG or Heart Rate. In step 504, patient 108 configures and operates the selected medical device to read a specific set of the patient's medical signs. In step 506, the medical device transmits and stores the selected patient medical signs on the information appliance 110. The electronic transmission may occur along either a direct or cordless connections electronic connection between medical device (e.g., 100, 102, 104 and 106) and information appliance 110. In either case, in step 510, the patient sends the medical data from the information device 110 to PHA 120. In step 512, the information appliance 110 displays the medical signs to patient 108. In step 518, PHA 120 receives the patient's medical signs and updates the database 130 with the entered data. The software of the PHA processes, classifies, categorizes and if selected, applies clinical management practice and/or clinical functions to the data. PHA 120, in step 516, electronically transmits the updated patient data in formatted reports to one or more designated health providers 136. The type and breadth of information a health provider 136 receives depends upon a number of factors including the health provider's information requirements and the configuration settings of the software of the system of FIG. 1. If a health provider 136 requires additional patient information, in step 524, the health provider 136 may electronically request additional information by sending a query to PHA 120.

Figure 16:
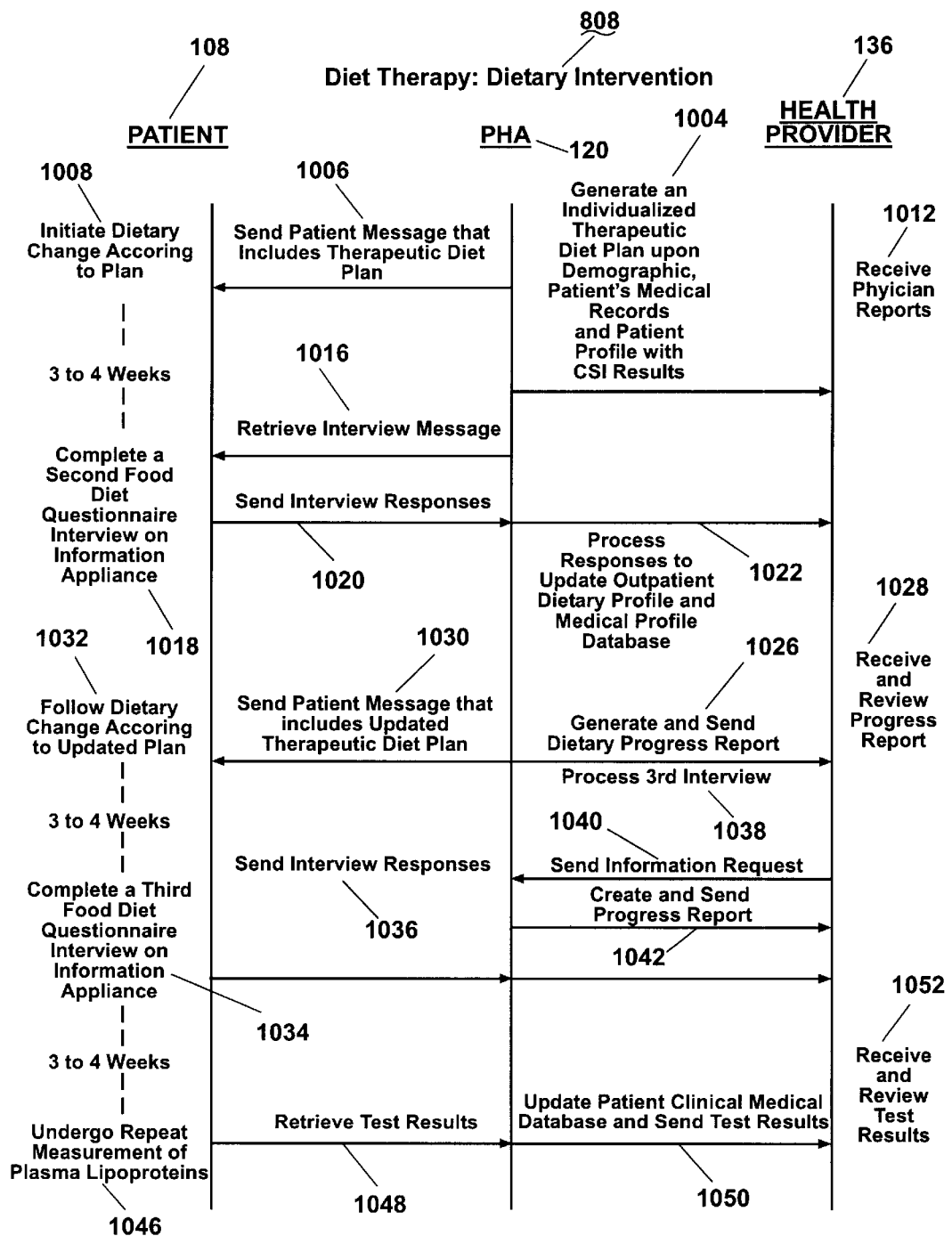
FIG. 16 is a flowchart showing an example of a "Dietary Intervention" phase of a "Diet Therapy" of FIG. 14.

Sign and symptom surveillance of FIG. 11 provides the nurse at a PHA 120, and a physician at a health provider 136 a means of closely monitoring volumes of patients. With close monitoring, the nurse and physician, may identify subtle changes of a patient's condition before the patient has an acute episode. Thus, the system of FIG. 16, provides preventative health care service without health providers 136 incurring added expense.

FIG. 11 illustrates a general application of the sign and symptom surveillance PHA 120 and one or more health providers 136 may use in a preferred embodiment of the present invention. In contrast, FIGS. 12–18 illustrate specific applications of the clinical related and clinical patient management functions supported by the system of FIG. 1. The breadth and scope of the examples demonstrate the configurable qualities of the clinical tele-informatics system.

Figure 12:
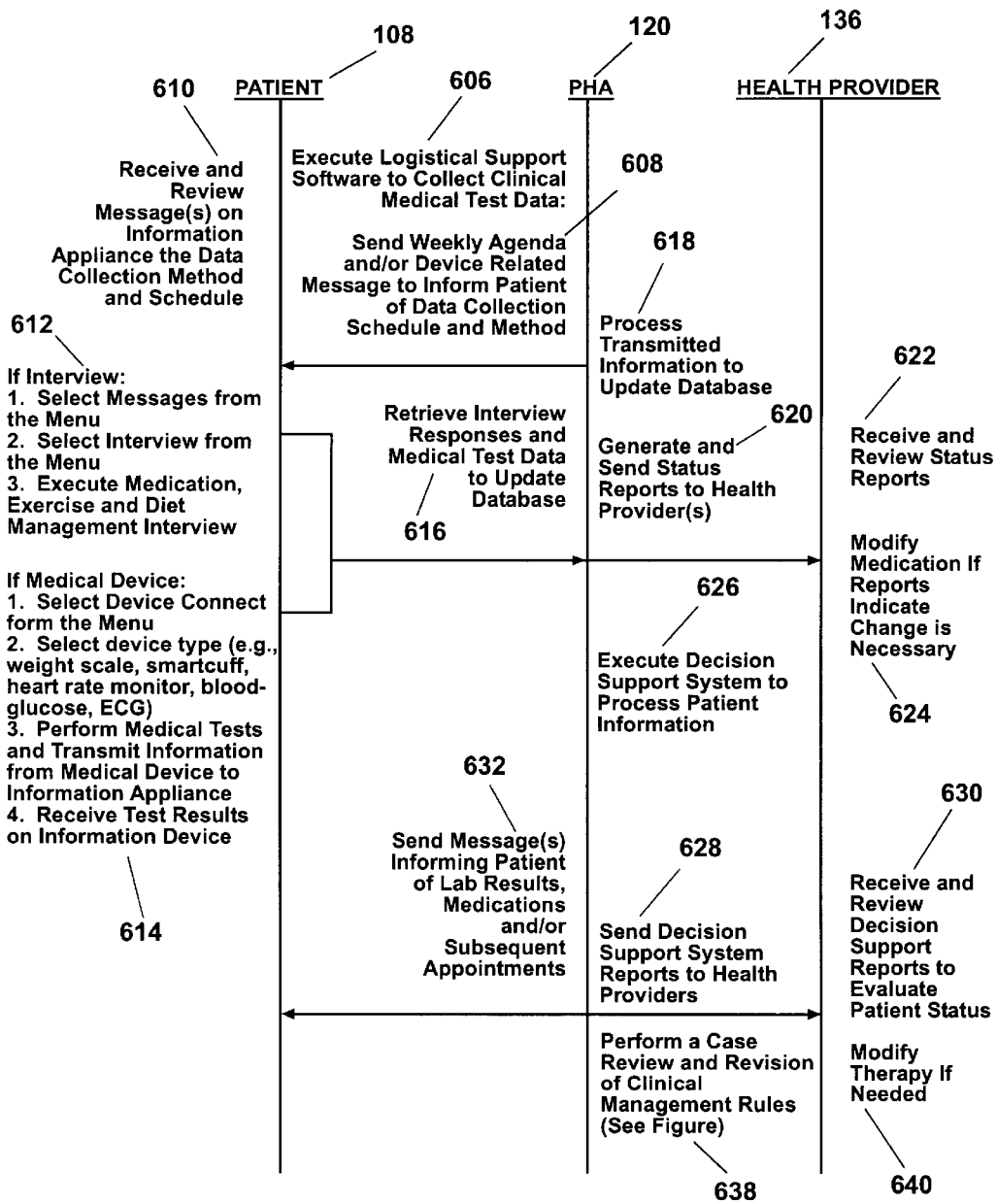
FIG. 12 is a flowchart showing a clinical services example of "Medication Management" provided by the system of FIG. 1.

FIG. 12 is a flowchart showing a clinical related example of "Medication Management" provided by the system of FIG. 1. It includes software that provides both logistical and decision support. The application assists the nurse at PHA 120 in recording a patient's medical history and physical examination results; following established treatment protocols; educating a patient about proper medicine dosages and potential side effects, administrating patient medication, instituting changes in drug therapies; and monitoring blood chemistries, side effects and therapy adherence. More specifically, FIG. 12 shows electronic communications between patient 108, a nurse at a PHA 120 and one or more health provider 136 sites during an initial twelve month period of managing a patient's medication. The example medication management of FIG. 12 shows "Lipids Management for Post-Myocardial Infarction Patients". This example shows the decision support software that includes treatment protocols which define niacin as the first drug of choice, followed by bile acid sequestrates, gemfibrozil, and lastly, lovastatin, often in combination with the preceding two drugs.

In the initial step of this process, PHA 120, in step 606, executes logistical support software. The nurse at PHA 120 determines and sends weekly agenda and/or device related messages 608 to inform the patient of "when", "how" and "what" patient 108 is to electronically transmit to PHA 120.

In a preferred embodiment, patient 108 enters and transmits medical condition information to PHA 120 with either an interview message or via a medical device (e.g., 100, 102, 104 and 106). In response to an interview message, in step 612, patient 108 selects "MESSAGES" from the menu of the information appliance 110. Next, patient 108 selects "INTERVIEWS" from the messages menu and then executes one or more electronic interviews provided by PHA 120. The electronic interviews reflect the therapies the patient currently receives such as medication, exercise and diet management. Patient 108, responds to each interview question. When the electronic interview ends when patient 108 completes entry of interview responses to the patient's satisfaction.

If patient 108 enters medical condition information via a medical device (100, 102, 104 and 106), in step 614, the patient selects "Device Connect" from the information appliance 110 menu. Next, patient 108 selects device type, such as weight scale, smartcuff, heart rate monitor, blood-glucose, ECG. Once operational, the medical device generates, sends and stores medical test readings of patient 108 on the information appliance 110. Patient 108 transmits the medical readings stored on the information appliance 110 to PHA 120.

Upon termination of the interviews and/or medical device tests, in step 616, PHA 120 receives and stores patient data on database 130. In step 618, PHA 120 processes, classifies and categorizes the data. In step 620, the PHA generates outpatient status reports for the PHA and for one or more designated health providers. The content of the information is determined by pre-selections of PHA 120 and health provider 136.

The health providers' immediate access to outpatient reports 622 is important, since current information of the patient's progress from one or more therapies may modify the recommended lipid-lowered drug therapy the patient currently receives, and may identify whether the patient is adhering to current therapies.

In step 624, a health provider 136 may in response to the outpatient clinical management reports alter the patient's drug therapy. Although not shown, a health provider 136 may electronically transmit the patient's modified drug therapy to PHA 120. If configured to receive reports, the nurse or an automated process of PHA 120 may send patient 108 an updated therapy described within a "MEDICATION MESSAGE".

After the patient enters and sends the information to PHA 120, decision support software 126 including clinical management functions performs analysis of the information according to a set of rules and factors, and determines a recommended drug therapy for patient 108. For example, in step 626, once PHA 120 receives the information, PHA 120 automatically executes decision support software 126 for lipid management of post-myocardial infarction patients based on clinical management rules stored in the system and five major factors. The major factors include lipid level, co-morbid conditions, blood chemistry, medical panels and side effects. After execution, PHA 120, in step 628, electronically sends the decision support results to one or more health providers and, in step 632, electronically sends a summarized report of the test results in simple language to patient 108. In step 630, the health providers 136 review the reports to evaluate the patient's drug therapy status. If necessary, a health provider 136 may modify the drug therapy recommended by the decision support results as shown at 640 and transmit the changes with an explanation to PHA 120 and patient 108 as described above.

The clinical management rules stored in the system designate a recommended set of therapies, including the drug therapy of FIG. 12, based on medical and medical related data a patient provides PHA 120. Since patient 108 regularly provides data of the patient's progress and reaction to therapies to PHA 120, therapies constantly improve, and new therapies become available, case review and revision of clinical management rules occur on a regular basis. In step 638, PHA 120 sends clinical management rules to individuals who are experts in the specific medical field, who are commonly referred to as domain experts. Domain experts possess expertise in the medical field pertaining to the outpatient's medical conditions and recommended therapies. The domain experts update and electronically return the clinical management rules to PHA 120.

Figure 13:
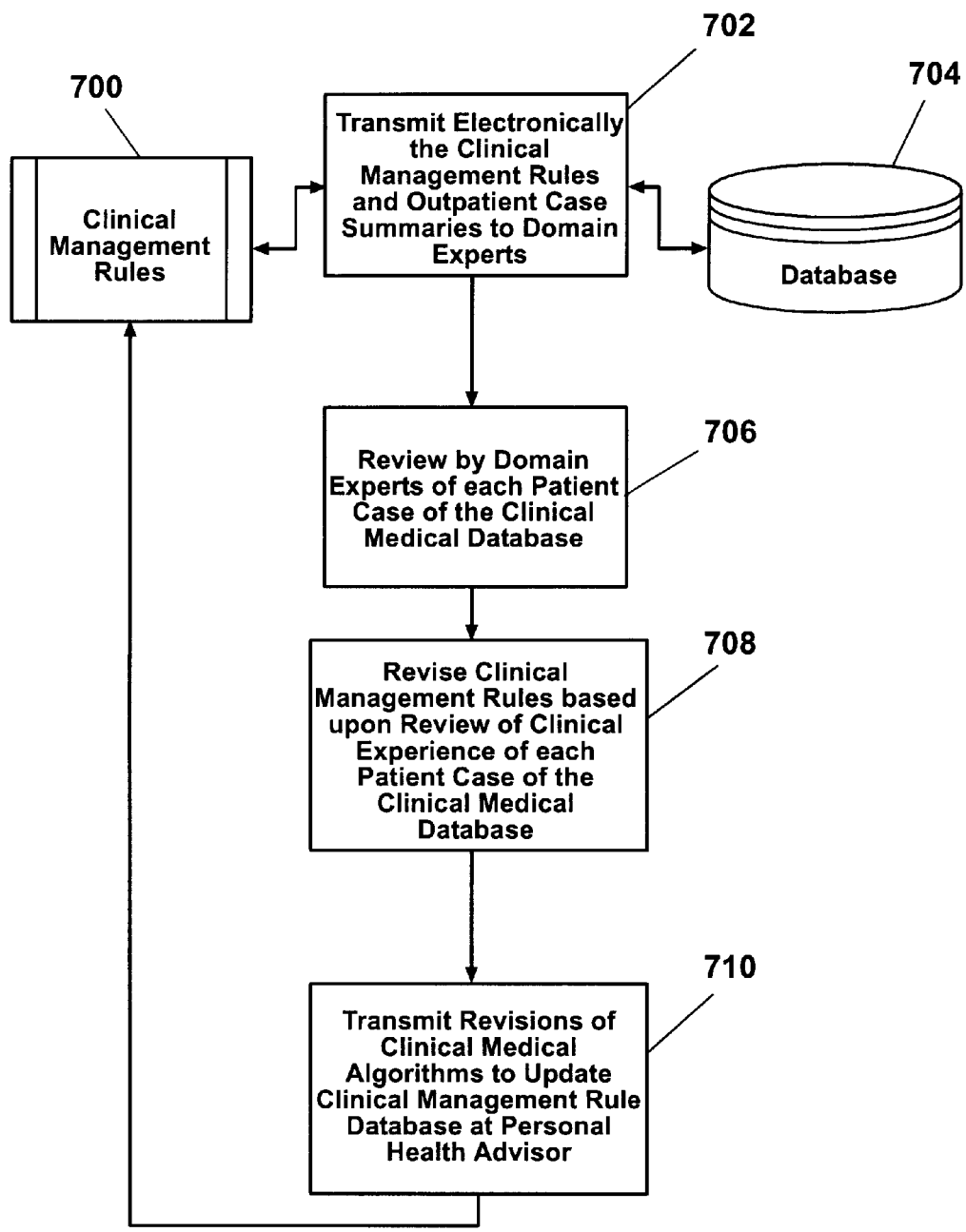
FIG. 13 is a flowchart showing an example of case review and revision of decision support clinical management rules of FIG. 12.

FIG. 13 is a flowchart showing in detail the case review and revision of decision support clinical management rules. In step 702, the nurse at a PHA 120 electronically transmits clinical management rules and out patient case summaries. The case summaries include specific medical data used to prescribe the outpatient's therapies and therapeutic results. For example, the case summary of a patient 108 under lipid management of post myocardial infarction includes changes in the patient's plasma lipoprotein values in response to currently prescribed therapies.

In a preferred embodiment PHA 120, at six month intervals, provides domain experts with outpatient case summaries from database 130 and clinical management rules. In step 706, the domain experts analyze this data. The analysis enables the domain experts to modify, in step 708, the current clinical management rules based on actual clinical experience acquired during the past six months of lipid-lowering drug therapy. Thus, clinical management rules may be individually tailored to each patient's electronically saved responses to specific therapies. For example, the therapies of a lipid-lowering patient 108 may include medication, diet, exercise and smoking. Each therapy may be modified according to a patient's therapeutic responses, so that a health provider 136 modifies current therapies to achieve maximum clinical effectiveness and diminish untoward therapy effects for patient 108. In step 710, the domain experts return the revised clinical management rules so that the nurse at PHA 120 and the health providers 136 may update and improve outpatient therapies.

Figure 14:
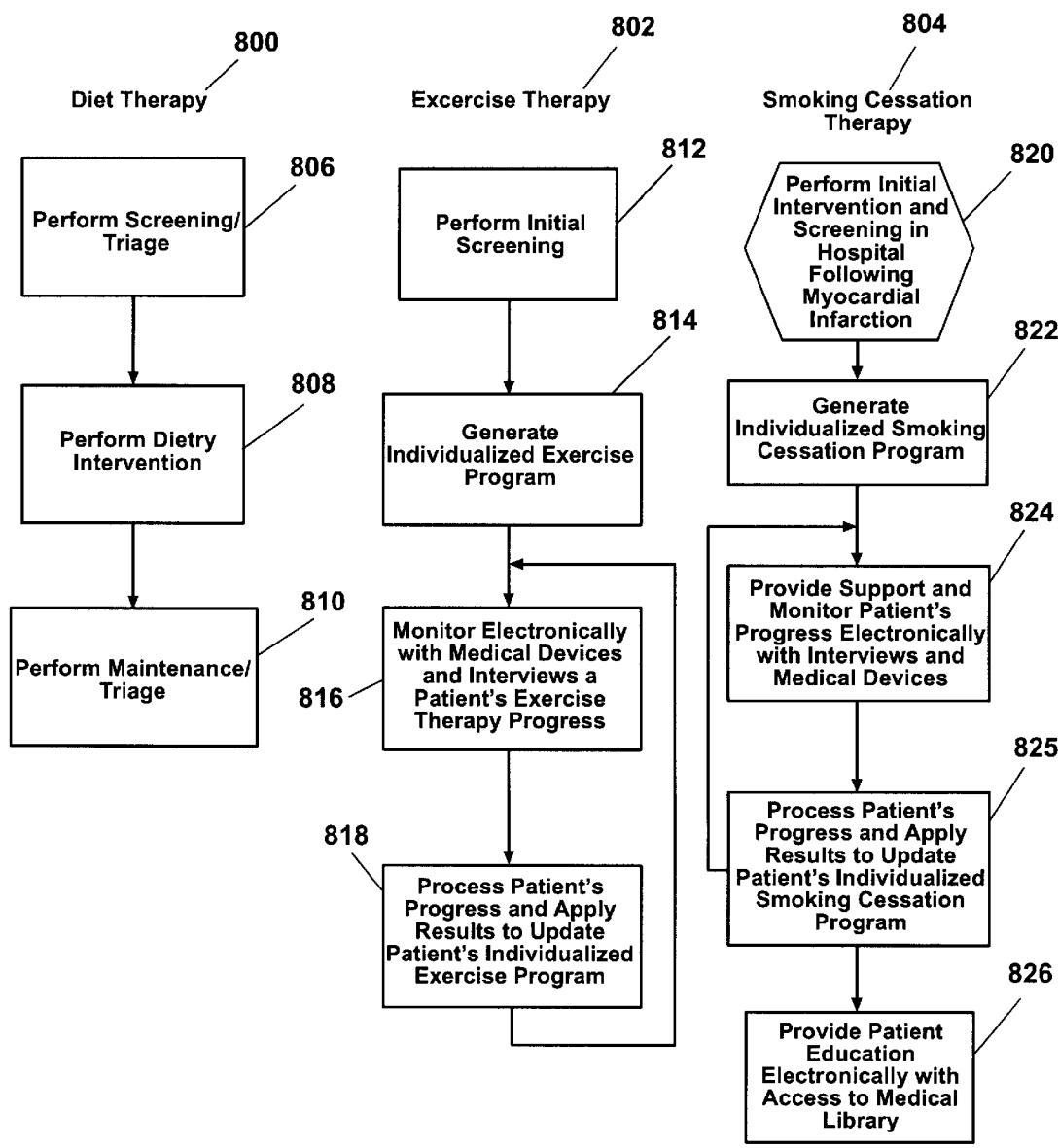
FIG. 14 is a flowchart showing an example of therapies provided by the system of FIG. 1.

FIG. 14 is a flowchart showing examples of risk factor modification therapies of post-myocardial infarction patients performed on the system of FIG. 1. The combination of diet, exercise and smoke cessation therapies demonstrate the system's support of comprehensive therapy treatment and clinical management for post-myocardial infarction patients. The example of a post myocardial patient and the recommended therapies of diet, exercise and smoking cessation are purely for illustrative purposes and should not be construed to limit the scope and application of this system to a wide variety of patient maladies and the corresponding recommended therapies.

The three example therapies of FIG. 14 for post-myocardial infarction patients are diet, exercise and smoking cessation. The diet therapy 800 is discussed in conjunction with detailed FIGS. 15, 16, and 17, and the remaining two example therapies of exercise and smoking cessation are shown in FIG. 14.

Now turning to diet therapy, research studies show that supplementing a drug therapy with an aggressive diet therapy may slow and reverse the arteriosclerosis of post-myocardial infarction patients. Conventional aggressive methods of dietary counseling often require numerous visits to a dietitian. In contrast, the system of FIG. 1 significantly reduces the need for these visits by providing patients 108 electronic access to a PHA 120 and a health provider 136 that supports individualized dietary goal setting and constant feedback from these medical professionals in reaching dietary goals.

Figure 17:
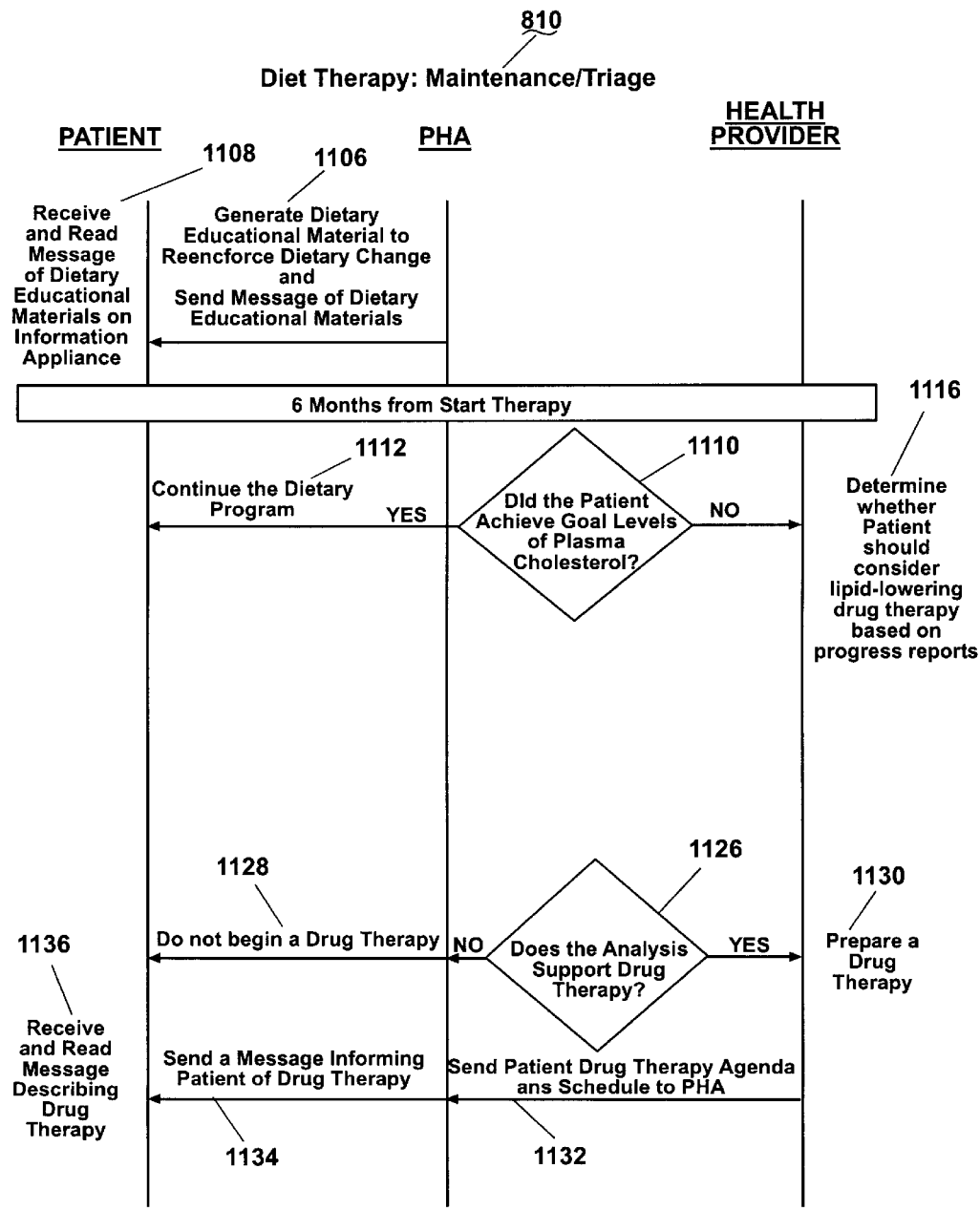
FIG. 17 is a flowchart showing an example of a "Maintenance/Triage" phase of a "Diet Therapy" of FIG. 14.

The three primary phases of diet therapy include the steps of performing screening and triage 806, performing dietary intervention 808, and performing maintenance and triage 810. Subsequent figures, FIGS. 15, 16, and 17 illustrate and explain in detail each dietary therapy phase.

Figure 15:
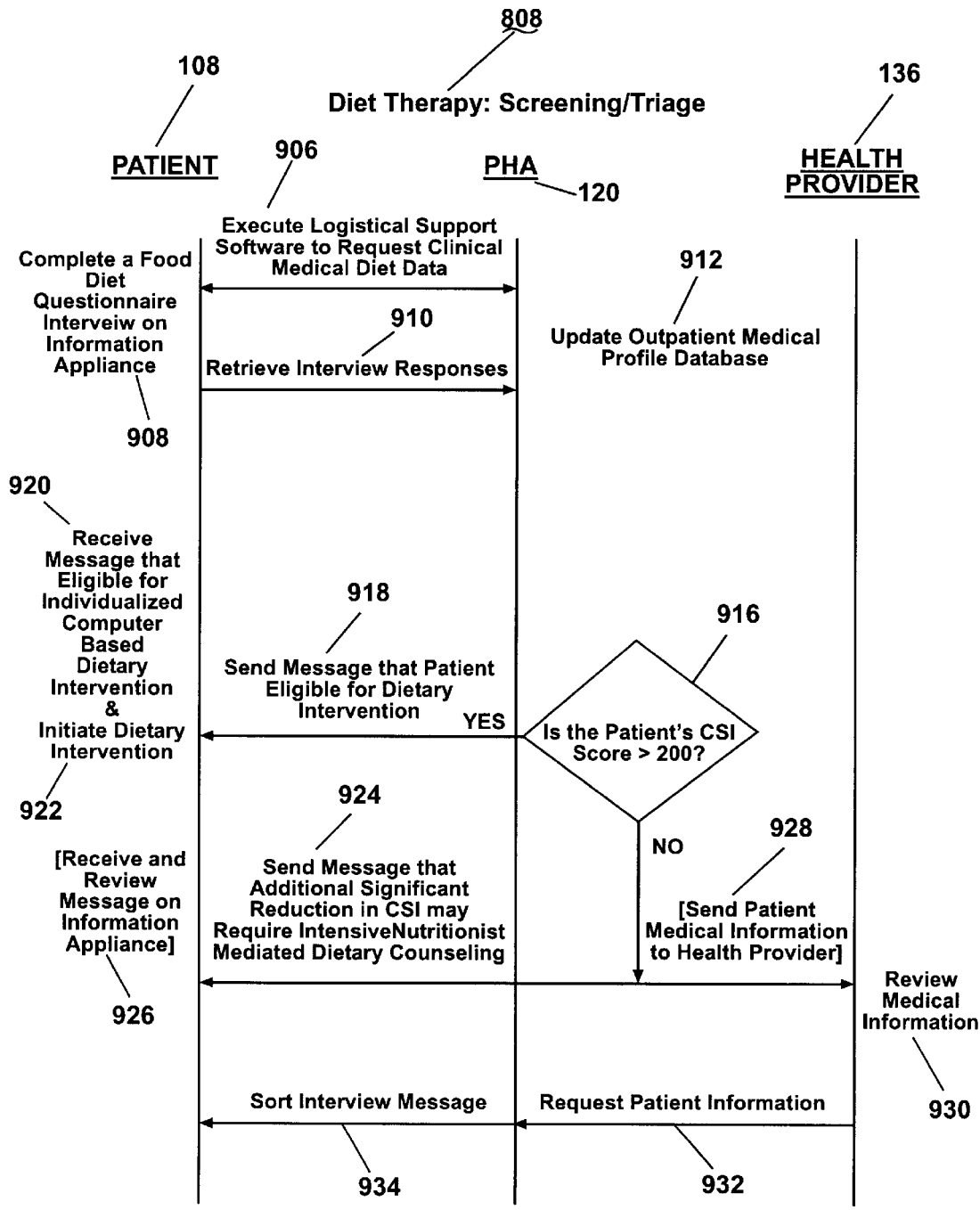
FIG. 15 is a flowchart showing an example of a "Screening/Triage" phase of a "Diet Therapy" of FIG. 14.

FIG. 15 is a flowchart showing an example of the "Screening/Triage" phase of the "Diet Therapy" of FIG. 14. This phase begins, in step 906, when the nurse at PHA 120 executes event manage software 128 to request clinical medical diet data from patient 108. Patient 108 retrieves on an information appliance 110 a "MESSAGE" of a food diet questionnaire interview. The questionnaire queries the patient via the information appliance 110 about the patient's dietary intake of the previous month. In step 908, patient 108 via the information appliance 110 accesses and responds to the "Interview Message" according to the steps of FIG. 9. In step 910, PHA 120 retrieves the patient's interview responses of step 908. In step 912, PHA 120 automatically stores the data on the database 130. In step 914, PHA 120 automatically processes the patient's responses using a food/cholesterol/fat/sodium database to produce a 15-component patient-specific profile of dietary cholesterol and saturated fat expressed as a Cholesterol Sodium Intake (CSI) score. The CSI score is an aggregate measure of the dietary cholesterol and saturated fat.

CSI scores over 200 generally reflect a dietary excess of cholesterol and saturated fat. In step 916, PHA 120 triages the patients into two groups, patients 108 with CSI scores above 200 and patients 108 with CSI scores of 200 or less. The distinction is made since a patient 108 with a CSI scores above 200 has the potential to substantially decrease plasma cholesterol while a patient 108 with a lesser score does not.

For a patient 108 with a CSI scores above 200, PHA 120, in step 918, electronically sends a message to patient 108 that the patient is eligible to receive dietary intervention. In step 920, patient 108 with a high CSI score receives the message, and in step 922, the patient initiates dietary intervention.

For patients with a CSI score of 200 or less, PHA 120 electronically sends patient 108 a message that a significant further reduction in dietary cholesterol and saturated fat may require intensive nutritionist-mediated dietary counseling. In step 926, the patient electronically receives and reviews the message on an information appliance 110.

In step 928, the dietary results of patient responses processed at PHA 120 are electronically sent to the designated health providers 136. In step 930, the designated health providers 136 review the results of the patient's dietary results. Based on the results, in step 932, a health provider 136 may electronically request that the nurse at PHA 120 obtain additional information from patient 108. In response, the nurse, in step 934, sends a new "Interview Message" to patient 108. The input and subsequent monitoring of a patient's interview responses will continue, until PHA 120 and the designated health providers 136 are satisfied that the screening/triage phase accurately classifies the patient's diet.

FIG. 16 is a flowchart showing an example "Dietary Intervention" phase of a "Diet Therapy" of FIG. 14. For a patient 108 with a CSI score above 200, patient 108 receives "dietary intervention", phase two of the dietary therapy. The PHA, in step 1004, generates an individualized therapeutic plan for patient 108 based upon demographic information and the outpatient's medical profile and responses to the food and diet interview. The individualized diet plan prioritizes objectives in changing a patient's diet and details the steps necessary to achieve that change. In step 1006, PHA 120 electronically sends the dietary plan coded in a "MESSAGE" to patient 108. Patient 108, in step 1008, receives and reviews the dietary plan on the patient's information device 110. Patient 108 may optionally print the dietary plan onto a hard-copy report. In a preferred embodiment, the dietary plan includes a 3 to 4 week diet schedule. In step 1012, one or more health providers 136 may electronically receive a copy of the patient's therapeutic plan.

In a preferred embodiment, the dietary plan incorporates a "Step Two American Heart Association" diet. However, alternative embodiment may incorporate other recommended diets that suit a patient's therapy needs.

After three to four weeks, PHA 120, in step 1016 sends patient 108 a "Message" of a second food diet questionnaire interview. In step 1018, the patient completes the second food diet questionnaire. In step 1020, PHA 120 retrieves the patient's responses of step 1018. PHA 120, in step 1022, processes the patient's response to update the outpatient dietary and medical profile databases. Processing of step 1026 generates a progress report that describes changes in the patient's dietary intake since initiation of the therapeutic plan and provides individualized instructions for further dietary change.

The PHA, in step 1030, electronically sends patient 108 the updated therapeutic dietary plan, and sends one or more health providers, in step 1026, the patient's dietary progress report. In a preferred embodiment, patient 108, in step 1032, receives the updated therapeutic dietary plan, and follows the plan. In step 1028 the designated health providers 136 receive and review the progress 10 report. A health provider 136, in step 1040, may request additional patient information either directly from patient 108 or from the nurse at PHA 120.

After three to four weeks, patient 108, in step 1034, electronically receives and responds to a third food diet questionnaire. Once PHA 120 retrieves patient 108 responses at step 1036 and then generates and sends a dietary progress report at step 1038, the dietary intervention process repeats the steps of the second food diet questionnaire interview for an additional cycle.

After three cycles of dietary intervention, for approximately 12 weeks, patient 108 undergoes repeat measurement of plasma lipoproteins at step 1046. If patient 108 has access to an appropriate medical device, patient 108 provides a plasma lipoprotein measurement by following the device connect steps of FIG. 11 discussed above. If the patient does not possess the device, the patient either has the nurse at PHA 120 or a health provider 136 measure the patient's lipoprotein level. If patient 108, in step 1048, electronically sends the results from the information appliance 110 to PHA 120, the decision support software 126 automatically processes and compares the patient's current lipoprotein levels to the levels prior to dietary intervention. The plasma lipoprotein measurements identify a patient's total cholesterol, LDL and HDL cholesterol and triglycerides. In step 1050, PHA 120 automatically sends the patient's comparative results to one or more designated health providers 136 where in step 1052, the designated health providers review and respond to the results.

FIG. 17 is a flowchart showing an example third phase, "Maintenance/Triage" of a "Diet Therapy" of FIG. 14. In a preferred embodiment, the dietary therapy of FIG. 14 includes a maintenance phase, since maximum clinical effectiveness occurs if dietary change is achieved during the 12 week "dietary intervention". More specifically, the National Cholesterol Educational Program (NCEP) recommends that at 6 months a therapeutics decision should be made as to whether a patient 108 should receive the lipid-lowering drug therapy shown in FIG. 15.

FIG. 17 shows a clinical tele-informatics system which supports the benefits of combining mutually conducive therapies. For example, this system supports the beneficial effects of combining drug therapy with dietary therapy. The system support for combining therapies is further exemplified below.

In step 1106, PHA 120 generates and sends dietary educational materials to a patient 108 to re-enforce the patient's dietary changes achieved during the first twelve weeks of the dietary intervention phase. In step 1108, the patient receives and reads the educational materials in a "MESSAGE" on an information appliance 110. Although not shown, a patient 108, may request as shown at step 1108 and as shown by the steps of FIG. 10, additional educational information from PHA 120.

Six months from the start of the diet therapy of FIG. 14, PHA decision support software 126 performs analysis, in step 1110, of the patient's 108 past six months of dietary change and lipoprotein values. In a preferred embodiment, the decision support software 126 evaluates patient data and recommends whether the patient should begin drug therapy. The software categorizes patients based upon therapeutic categories established by the National Cholesterol Educational Program (NCEP). Patient categorization is based upon information such as the patient's gender, history of hypertension, smoking, diabetes or clinically evident ischemic heart disease, values of HDL cholesterol and family history.

In step 1110, if decision support 126 analysis determines that a patient 108 achieved the patient's goal level of plasma cholesterol, PHA 120 in step 112 sends patient 108 a "MESSAGE" to continue the current dietary plan, and sends the designated health providers 136 a report of the positive results.

If, however, patient 108 did not achieve the patient's goal level of plasma cholesterol, the designated health providers 136 receive a health provider report at step 1116 of the patient's progress which identifies the negative results. In a preferred embodiment, the progress reports include the patient's therapeutic category, the extensive list of information used to classify patient 108, and a recommendation of whether the patient should consider lipid lowering drug therapy.

If, in step 1126, the health provider 136 follows the decision support software 126 recommendation to begin drug therapy, the health provider 136, in step 1130 prepares the patient's drug therapy. At step 1132 the health provider 136 sends the patient's 108 drug therapy agenda and schedule to PHA 120. In step 1134, PHA 120 sends patient 108 a "MESSAGE" recommending that patient 108 begin drug therapy. In step 1136, the patient receives and reads the "message" describing the drug therapy, including the agenda and schedule, on the patient's information device 110.

If the analysis of the PHA decision support software 126 and a health provider 136 do not recommend drug therapy, in step 1128, PHA 120, sends patient 108 a message to continue current therapies such as a dietary program. Further, PHA 120 may electronically send the patient's decision support reports and medical profiles to the domain experts, and request that the experts perform a comprehensive review of the patient's condition.

FIGS. 15, 16 and 17 illustrate in detail the three primary phases of the diet therapy of FIG. 14. The figures illustrate an example of one of the benefits of the integrated clinical tele-informatics system of FIG. 1 which is the comprehensive therapeutic approach the system provides a patient by systemically combining, balancing and modifying a plurality of therapies according to routine measurements of the patient's medical condition.

Now returning to FIG. 14, a plurality of therapies may supplement a diet therapy such as an exercise therapy 802 and a smoking cessation therapy 804. Exercise therapy 802, for example, is designed to increase the patient's functional capacity. A systematic approach to this therapy provides specific instructions for walking and other exercise based on extensive testing during an initial screening phase. For example, in step 812, the patient receives treadmill and other initial screening tests to determine the patient's medical condition. In a preferred embodiment, patient 108 has medical testing devices 100, 102, 104, 106 so that in step 812, the patient performs physical health tests and electronically transmits results of the via the "Device Connect" Menu of the information appliance 110, as discussed above. In step 814, event manager software 128 and the database software 134 store the data in database 130. Event manager 128 and the decision support software 126 classify and categorize the data to update the patient's electronic record, and then process the data to generate and send to patient 108 an individualized exercise program.

Patient 108, in step 816, provides the PHA his or her heart rate monitor readings throughout the prescribed exercise program. Further, the patient executes "MESSAGE" interviews to log therapy activity and to answer PHA electronic questions.

At first, the nurse of PHA 120 conducts weekly electronic interviews with the patient. However, if patient 108 is progressing well, interviews occur less frequently, such as on a monthly basis. In step 818, PHA 120 retrieves the patient's interview responses. PHA 120 processes the interview responses and medical device readings to determine the patient's therapeutic progress and update the patient's individualized exercise program. Although, not shown, the designated health providers 136 receive status reports of patient's condition and patient's adherence to the prescribed therapy. Further, PHA 120 provides clinical management functions to convert patient data to value added information in configurable formats that may be entered into PHA and health provider reports.

In addition to exercise therapy 802, smoking cessation therapy 804 of a patient 108 who continues to smoke after a myocardial infarction is necessary, since a patient's mortality rate for those that continue to smoke is statistically much hither than if the patient stops smoking. Research has suggested that approximately one-half of the patients who smoked prior to having an infarction resume smoking within 6 months after the infarction. Therefore, a preferred embodiment of the smoking cessation therapy occurs for a period of one year.

FIG. 14 shows, in step 820, the initial intervention and screening that occurs in the hospital immediately following an infarction. The step involves a period of enforced smoking cessation. Based on a social learning theory, the intervention is directed toward relapse prevention training. For example, nicotine replacement therapy is used if patient 108 is at risk of a relapse, since patient 108 believes she is unable to cope with the urge to smoke. In step 822, patient 108, while at the hospital, responds to a serious of interview questions. The PHA processes the responses to categorize the patient in a risk group based upon her risk of relapse. For each risk group category, patient 108, in step 822, receives an individualized smoking cessation program that includes a specific set of therapies tailored to address the patient's risk of relapse.

Once the patient returns home, the system of FIG. 1 electronically provides support and monitors the patient's progress. For example, in step 824, patient 108 at predetermined time periods established by the system's agenda and scheduling functions electronically provides interview responses and medical device readings to PHA 120. The event manager software 128 updates the database 130 with the patient data. The PHA's decision support software 126 and database software 134, in step 826, automatically analyzes the patient's interview responses and medical device readings to track the patient's progress, and if necessary to update her individualized smoking cessation program. The updates are entered into the patients database record.

The system of FIG. 14, also provides a patient 108, in step 826, access to education materials to answer the patients questions and reinforce the patients resolve to terminate smoking. If, however, patient 108 resumes smoking, the program recommends that patient 108 receive additional face to face counseling session with PHA 120 or a health provider 136.

Figure 18:
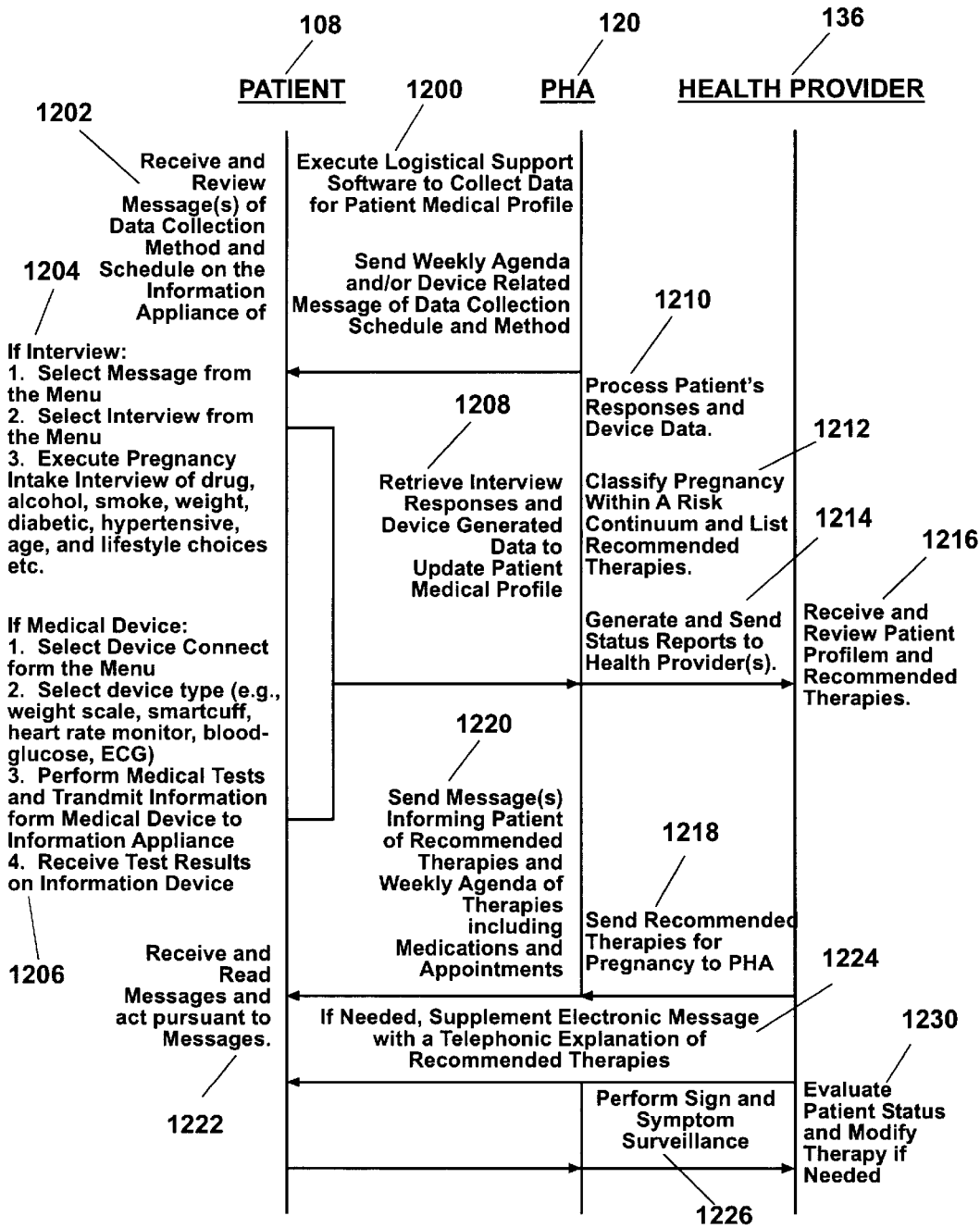
FIG. 18 is a flowchart showing an example of Clinical Management, Patient Classification and Therapy Assignment for Pregnancy provided by the system of FIG. 1.

FIG. 18 is a flowchart showing an example of clinical management, patient classification and therapy assignment for a pregnancy. Similar to the systematic steps for a post-myocardial infarction patient, shown in FIGS., 12–16, PHA 120, in step 1200, first executes event manager software 128 to collect patient medical data to create a patient medical profile. PHA 120 sends in a "MESSAGE", weekly agenda and device related messages to inform patient 108 of the planned methods and schedules for data collection.

In step 1202, patient 108 receives and reviews, in accordance with the steps of FIG. 8, the informative "Messages" on their information appliance 110. If patient 108 responds to an interview, in step 1204, she selects the "MESSAGES" option from the menu on her information appliance 110. Then, patient 108 selects "Interview" from the "Menu." Next, the patient executes and responds to a pregnancy intake interview. Example question topics include drug, alcohol, and smoke use; weight and age; whether the patient is diabetic or hypertensive, and a patient's lifestyle choices.

If the patient enters medical device readings, in step 1206, the patient follows the four step process shown in FIG. 18.

In step 1208, PHA 120 retrieves the patient's 108 interview responses and medical device readings and stores the data in a database 130. The PHA decision support 126 and event manager 128 software, in step 1210, automatically processes the responses and device data, and in step 1212, classifies the pregnancy within a risk continuum based upon the available information and clinical management rules. In a preferred embodiment, the risk continuum is divided into at least three risk classifications of normal, medium or high risk. The software recommends for patient 108 a specific set of therapies based upon the patient's classification in the risk continuum. Generally, the number of recommended therapies is directly proportional to a patient's classification in the risk continuum. Thus, high risk patients receive significantly more therapies in contrast to low risk patients.

In step 1216, PHA 120 automatically sends a patient's medical profile and recommended therapies to one or more health providers 136. The designated health providers 136 review the reports and in step 1218 send PHA 120 a "MESSAGE" if there are changes to the recommended therapies. Although not shown, the designated health providers 136 may request additional patient information. In step 1220, PHA 120 electronically sends "MESSAGES" informing the patent 108 of recommended therapies and the weekly agenda for each therapy. The "MESSAGES" provide information such as prescribed medication and appointments. In step 1222, patient 108 receives and reads the messages.

If patient 108 requires an explanation of the recommended therapies or if PHA 120, or designated health providers 136 wish to supply supplemental information, in step 1224, the parties use the "Messaging" functions of the system of FIG. 1 to communicate the requests and responses.

Once a patient initiates the patient's therapies, in step 1226, PHA 120 executes sign and symptom surveillance, with patient 108 and designated health providers 136 for the term of the pregnancy. As discussed with regard to post-myocardial patients 108, the patient's set of recommended therapies may change in response to the patient's condition throughout the pregnancy term.

Several preferred embodiments of the present invention have been described. It will be understood that various modifications may be made without departing from the spirit and scope of the invention.

In describing the preferred embodiments, a number of specific technologies used to implement the embodiments of various aspects of the invention were identified and related to more general terms in which the invention was described.

It should be understood, however, that such specificity is not intended to limit the scope of the claimed invention.

What is claimed is:

1. A tele-informatics system for providing clinical case and clinical practice management service comprising:

a plurality of information appliances configured for deployment at locations remote from a central location for use by a corresponding plurality of patients, each appliance having a respective data entry device and an alpha-numeric display;

a Personal Health Advisor ("PHA") configured for deployment at said central location, said information appliances and said PHA in selective two-way communications with one another, said information appliances and said PHA being configured to transmit and receive data from each other, each of said information appliances selectively generating data by means of said data entry device which is received by said PHA, said PHA including a computer for analyzing said data and generating a plurality of responses which are received by said alpha-numeric display of said information appliances to provide clinical practice management for the plurality of patients; and wherein said PHA further includes an event manager executing on said computer configured to generate a clinical agenda based on a comparative analysis of said data provided by said plurality of patients, said clinical agenda prioritizing timing of patient care.

2. A system as recited in claim 1, wherein said data entry device includes at least one of weight scale, heart monitor, blood sugar monitor, and pulse monitor.

3. A system as recited in claim 2, wherein said clinical practice management includes a first portion configured to accept said data; and a second portion configured to analyze said data according to a plurality of clinical case management rules.

4. A system as recited in claim 1, wherein said event manager generates an alert when said data from at least one of said plurality of patients exceeds a predefined medical parameter defined by said clinical case management rules.

5. A system as recited in claim 4, wherein at least one of said responses includes a request to schedule a subsequent activity as defined by said clinical case management rules.

6. A system as recited in claim 5, wherein at least one of said responses includes a plurality of queries to be completed by the patient to whom said one response is directed to provide additional amounts of said data.

7. A system as recited in claim 6, wherein said PHA further includes a decision support manager to generate therapy information of recommended treatments based upon an analysis of said data and transmitting said therapy information through said responses to said information appliances.

8. A system as recited in claim 1, including a health provider, said health provider using said data to determine trends among those patients having similar conditions.

9. A tele-informatics system for providing outpatient health care delivery, self-care services, clinical communications and information, and clinical practice management services comprising a personal health advisor ("PHA") including:

a medical data portion configured to accept medical data from a plurality of patients;

a clinical information portion configured to analyze said medical data entered in said medical data portion according to a plurality of clinical case management rules;

a therapy response portion configured to respectively assign the patients at least one therapy responsive to said clinical information portion;

a monitoring portion configured to monitor updated data from each of the patients and to update said clinical information portion and said therapy response portion in response to said updated data; and wherein said PHA further includes an event manager executing on a computer and configured to generate a clinical agenda based on a comparative analysis of said medical data received by said medical data portion, said clinical agenda prioritizing timing of patient care.

10. The system as recited in claim 9, further comprising a plurality of information appliances respectively located by the patients, said information appliances being respectively configured to generate said data received by said medical data portion of said PHA, receive alphanumeric messages, and key responses to queries generated by said PHA.

11. The system as recited in claim 9, wherein said monitoring portion further includes:

a portion configured to modify said clinical case management rules according to at least one of (i) historical responses of the patients to therapy and (ii) revision by an expert; and a portion configured to modify, for at least one of said patients, a respective therapy according to one of said updated data and said modified clinical case management rules.

12. A method for providing a communications tele-informatics system for providing outpatient health care delivery, patient self-care services, clinical communications and information, and clinical practice management services, said method comprising the following steps performed by a Personal Health Advisor, of:

retrieving medical data from a plurality of patients;

generating a triaged clinical agenda from a comparative analysis of said medical data to thereby prioritize a PHA response to each patient's health care needs;

analyzing said medical data according to a plurality of clinical case management rules;

generating clinical case management information for each patient from said analyzing step;

assigning, for each patient, at least one therapy responsive to said generating step; and sending, to each patient, the at least one therapy of the assigning step in accordance with the triaged clinical agenda.

13. The method recited in claim 12, comprising the step of modifying said clinical case management rules based on said case management information from the plurality of patients.

14. The method recited in claim 12, comprising the steps of sending to at least one of the patients a message enclosing a schedule to enter said medical data into an information device;

monitoring updated medical data from said information device;

analyzing said updated medical data;

generating a clinical information update of the at least one patient; and updating said therapy associated with said at least one patient when said clinical information update differs from said clinical information.

15. The method of claim 12, comprising the step of providing at least one of the patients health care education, said health care education including access to medical libraries, medical terminology, and explanations of said therapy associated with said at least one patient.

16. The method as recited in claim 12, further comprising the steps, performed by at least one of the patients, of:

generating said medical data;

storing said medical data into an information device; and receiving said therapy associated with said at least one patient in response to said sending step.

17. The method as recited in claim 16, performed by at least one of the patients, wherein said data of said medical data generating step is provided by one of responses to an interview and readings from a medical device.

18. A method as recited in claim 12, further comprising the step, performed by a health provider, of:

responding in accordance with the triaged clinical agenda.

19. A tele-informatics system for providing clinical case and clinical practice management services comprising:

a plurality of information appliances configured for deployment at locations remote from a central location for use by a corresponding plurality of patients, each appliance having a respective data entry device and an alpha-numeric display; and a Personal Health Advisor ("PHA") configured for deployment at said central location, said information appliances and said PHA in selective two-way communications with one another, said information appliances and said PHA being configured to transmit and receive data from each other, each of said information appliances selectively generating data by means of said data entry device which is received by said PHA, said PHA including a computer for analyzing said data and generating a plurality of responses which are received by said alpha-numeric display of said information appliances to provide clinical practice management for the plurality of patients, said PHA further including a medical data portion configured to accept medical data from the plurality of patients, a clinical information portion configured to analyze said medical data entered in said medical data portion according to a plurality of clinical case management rules, a therapy response portion configured to respectively assign the patient at least one therapy responsive to said clinical information portion, and a monitoring portion configured to monitor updated data from each of the patients and to update said clinical information portion and said therapy response portion in response to said updated information wherein said PHA further includes an event manager executing on said computer configured to generate a clinical agenda based on a comparative analysis of said data provided by said plurality of patients, said clinical agenda prioritizing timing of patient care.

20. A tele-informatics system as recited in claim 19, wherein said data entry device includes at least one of a weight scale, heart monitor, blood sugar monitor, and pulse monitor;

said clinical practice management includes a first portion configured to accept said data; and a second portion configured to analyze said data according to a plurality of clinical case management rules;

said event manager generating an alert when said data exceeds a predefined medical parameter defined by said clinical case management rules;

at least one of said responses including a request to schedule a subsequent activity as defined by said clinical case management rules;

at least one of said responses including a plurality of queries to be completed by the patient to whom the queries are directed to provide additional amounts of said data;

a decision support manager to generate therapy information of recommended treatments based upon an analysis of said data and transmitting said therapy information through said responses to said information appliances; and a health provider having medical knowledge, said health provider using said data to determine trends among those patients having similar conditions.

* * * * *